(12) United States Patent
Cano et al.

(10) Patent No.: US 7,355,087 B2
(45) Date of Patent: Apr. 8, 2008

(54) PRODUCTION OF 1-ALKENES FROM MIXED OLEFIN STREAMS USING CATALYTIC DISTILLATION

(75) Inventors: Manuel Luis Cano, Houston, TX (US); David Morris Hamilton, Jr., Sugar Land, TX (US); Terry Blane Thomason, Houston, TX (US)

(73) Assignee: Shell Oil Company, Houston, TX (US)

( * ) Notice: Subject to any disclaimer, the term of this patent is extended or adjusted under 35 U.S.C. 154(b) by 617 days.

(21) Appl. No.: 10/957,237

(22) Filed: Oct. 1, 2004

(65) Prior Publication Data

US 2005/0080309 A1 Apr. 14, 2005

Related U.S. Application Data

(60) Provisional application No. 60/508,231, filed on Oct. 2, 2003.

(51) Int. Cl.
*C07C 5/23* (2006.01)
*C07C 7/17* (2006.01)

(52) U.S. Cl. .............. 585/664; 585/665; 585/666; 585/667; 585/668; 585/669; 585/670; 585/857; 585/860; 585/862; 585/864; 585/866

(58) Field of Classification Search ........ 585/664–670, 585/857, 860, 862, 864, 866
See application file for complete search history.

(56) References Cited

U.S. PATENT DOCUMENTS

| | | | |
|---|---|---|---|
| 4,727,203 A | 2/1988 | Hamilton, Jr. ........... 585/329 |
| 4,749,819 A | 6/1988 | Hamilton, Jr. ........... 585/329 |
| 4,797,133 A | 1/1989 | Pujado ..................... 44/53 |
| 4,895,997 A | 1/1990 | Hamilton, Jr. et al. ..... 585/329 |
| 4,915,794 A | 4/1990 | Slaugh et al. ............ 203/29 |
| 4,962,267 A | 10/1990 | Slaugh ..................... 585/670 |
| 4,996,386 A | 2/1991 | Hamilton, Jr. et al. ..... 585/646 |
| 5,008,480 A | 4/1991 | Slaugh ..................... 585/323 |
| 5,030,792 A | 7/1991 | Slaugh ..................... 585/639 |
| 5,043,520 A | 8/1991 | Hamilton, Jr. ............ 585/646 |
| 5,087,780 A | 2/1992 | Arganbright .............. 585/259 |
| 6,156,947 A | 12/2000 | Vora ....................... 585/324 |
| 6,166,279 A * | 12/2000 | Schwab et al. ........... 585/324 |
| 6,768,038 B2 * | 7/2004 | Powers .................... 585/664 |

FOREIGN PATENT DOCUMENTS

| | | |
|---|---|---|
| WO | 02/059066 | 8/2002 |
| WO | 02/096843 A1 | 12/2002 |

OTHER PUBLICATIONS

"Review of Olefin Isomerization", H.N. Dunning, Industrial and Engineering Chemistry, 45, 551-564 (1953).
International Search Report of Feb. 25, 2005.
Written Opinion of PCT/US2004/032273 of Feb. 25, 2004.

* cited by examiner

*Primary Examiner*—Glenn Caldarola
*Assistant Examiner*—In Suk Bullock

(57) ABSTRACT

A catalytic distillation process for isomerizing and separating 1-alkenes from a mixed alkene stream. The process comprises contacting a mixed alkene stream comprising the 1-alkene and homologs thereof with a supported isomerization catalyst under isomerization/distillation conditions effective to convert at least a portion of the homologs to the 1-alkene, the isomerization/distillation conditions also being effective to produce a distillation overhead comprising a sufficient portion of the 1-alkene to drive isomerization of the homologs to the 1-alkene while maintaining the mixed alkene stream at least partially in liquid phase. The isomerization/distillation conditions are effective to recover a quantity of 1-alkene greater than an equilibrium quantity of 1-alkene recovered under isomerization conditions alone. The 1-alkene is selected from the group consisting of 1-alkenes having from about 4 to about 8 carbon atoms; provided that, when the mixed alkene stream is a $C_4$ stream, the isomerization/distillation conditions comprise an amount of an extraction agent.

162 Claims, No Drawings

PRODUCTION OF 1-ALKENES FROM MIXED OLEFIN STREAMS USING CATALYTIC DISTILLATION

This application claims the benefit of U.S. Provisional Application No. 60/508,231 filed Oct. 2, 2003, the entire disclosure of which is hereby incorporated by reference.

FIELD

The application relates to novel catalytic distillation methods for the production of 1-alkenes. Preferably, the alkenes have from 4 to 8 carbon atoms, more preferably from 5 to 8 carbon atoms, even more preferably 5 or 6 carbon atoms.

BACKGROUND

Mixed alkenes generally are less valuable than 1-alkenes. Methods always are needed to recover 1-alkenes from mixed alkenes.

SUMMARY

The application provides a method for producing a distillation overhead comprising a 1-alkene. The method comprises contacting a mixed alkene stream comprising the 1-alkene and homologs thereof with a supported isomerization catalyst under isomerization/distillation conditions effective to convert at least a portion of the homologs to the 1-alkene, the isomerization/distillation conditions also being effective to produce a distillation overhead comprising a sufficient portion of the 1-alkene to drive isomerization of the homologs to the 1-alkene while maintaining the mixed alkene stream at least partially in liquid phase. The isomerization/distillation conditions are effective to recover a quantity of 1-alkene greater than an equilibrium quantity of 1-alkene recovered under isomerization conditions alone. The 1-alkene is selected from the group consisting of 1-alkenes having from about 4 to about 8 carbon atoms; provided that, when the mixed alkene stream is a $C_4$ stream, the isomerization/distillation conditions comprise an amount of an extraction agent.

DETAILED DESCRIPTION

The present application provides a catalytic distillation process for producing and separating a 1-alkene from a mixed alkene stream, preferably produced by isomerization.

The Alkenes

A variety of mixed alkenes may be separated using the catalytic distillation process as long as a sufficient differential exists between the boiling point of the 1-alkene and the boiling point of homologous alkenes to separate the 1-alkene by the selected distillation process.

1-butene is separable from a $C_4$ mixed alkene stream by conventional distillation. See U.S. Pat. No. 5,087,780, incorporated herein by reference. The data in the following Tables demonstrate that the 1-alkene isomer and homologous isomers of molecules having from about 5 to about 8 carbon atoms also have a sufficient boiling point differential to permit separation by conventional distillation:

| Carbon Number | Compound | BP (° C.) | BP (° C.) versus Homologous 1-Alkene |
|---|---|---|---|
| C5's | n-pentane | 36.0 | 6.1 |
| | 1-pentene | 29.9 | 0.0 |
| | trans-2-pentene | 36.3 | 6.4 |
| | cis-2-pentene | 36.9 | 7.0 |
| C6's | n-hexane | 68.7 | 5.3 |
| | 1-hexene | 63.4 | 0.0 |
| | trans-2-hexene | 67.9 | 4.5 |
| | cis-2-hexene | 68.8 | 5.4 |
| | trans-3-hexene | 66.4 | 3.0 |
| | cis-3-hexene | 67.1 | 3.7 |
| C7's | 1-heptane | 98.5 | 4.9 |
| | 1-heptene | 93.6 | 0.0 |
| | trans-2-heptene | 98.0 | 4.4 |
| | cis-2-heptene | 98.4 | 4.8 |
| | trans-3-heptene | 95.7 | 2.1 |
| | cis-3-heptene | 95.8 | 2.2 |
| C8's | n-octane | 125.6 | 4.4 |
| | 1-octene | 121.2 | 0.0 |
| | Trans-2-octene | 125.0 | 3.6 |
| | cis-2-octene | 125.6 | 4.2 |
| | Trans-3-octene | 123.3 | 1.9 |
| | Trans-4-octene | 122.3 | 0.9 |
| | cis-4-octene | 122.5 | 1.1 |

The boiling point differentials between homologous alkenes become small when the number of carbon atoms is greater than 8, as seen in the Table below:

| Carbon Number | Compound | BP (° C.) | BP (° C.) versus Homologous 1-Alkene |
|---|---|---|---|
| C9's | n-nonane | 150.8 | 3.9 |
| | 1-nonene | 146.9 | 0.0 |
| | trans-3-nonene | 147.5 | 0.6 |
| C10's | n-decane | 174.1 | 3.6 |
| | 1-decene | 170.5 | 0.0 |
| | trans-4-decene | 170.6 | 0.1 |
| | cis-4-decene | 170.6 | 0.1 |
| | trans-5-decene | 171 | 0.5 |
| | cis-5-decene | 171 | 0.5 |

Based on the foregoing, preferred 1-alkenes for separation using conventional distillation and/or extractive distillation have 5 or 6 carbon atoms. Because of the small boiling point differential between the 1-alkene and homologous alkenes in $C_7$ and $C_8$ streams, it may be desirable to enhance the separation. A preferred method of enhancing separation is extractive distillation.

Isomerization/Distillation

Isomerization is catalytically activated. The isomerization reaction is reversible. When an isomerized olefin feed stream is at equilibrium, the concentration of 1-alkene in the equilibrium mixture varies depending upon conditions and the alkene mixture, but generally is low. Distillation removes the 1-alkene continuously from the reaction zone, driving the isomerization away from equilibrium and producing more 1-alkene than would be obtained in an equilibrium reactor (fixed bed flow through) in the absence of the isomerization catalyst.

The isomerization reaction produces an isomerized mixture of alkenes, primarily alpha olefins (AO) or internal olefins (IO), which are separated into AO and IO fractions, preferably in the same column. Some impurities, such as dienes, may be produced depending upon the feedstream. The distillation process separates the AO and the IO. The distillation process to separate the AO from the IO may be conventional distillation, which works purely by boiling point differences, and/or extractive distillation by which another component is added to the distillation column and this component interacts (but does not "react") with the AO and IO to change their relative volatilities. Because a catalyst is necessary for the isomerization process, both types of distillation are hereafter referred to as "catalytic distillation" processes. Preferably the catalytic distillation process produces an overhead comprising alkenes consisting essentially of the desired 1-alkene.

Suitable isomerization catalysts for use in the catalytic distillation reaction are any of the well known isomerization catalysts which promote double bond isomerization with little or no concurrent polymerization or cracking; however, the catalyst must be in a form adapted to serve as distillation packing. The reaction system is heterogeneous since the catalyst remains as a distinct entity.

The isomerization catalyst preferably comprises a support having substantially any morphology effective to provide the desired surface area and flow through the distillation column. Generally, the surface area must expose a sufficient amount of the catalyst to produce a commercially acceptable, or effective reaction rate. Since the porosity or available internal surface area will vary for different support materials, the optimum particle size of the support will vary. Suitable supports include, but are not necessarily limited to extrudates, structured packing devices, monolithic supports, ceramic foams, and reticulated polymer foams comprising cells sufficiently large to prevent high pressure drops through the distillation column and to allow effective vapor flow. Suitable support morphologies include, but are not necessarily limited to rings, saddles, balls, irregular, cylinders, multilobed structures, sheets, tubes, spirals, packed bags, grills, screens, ceramic foams, and reticulated polymer foams. Preferred support morphologies are selected from the group consisting of Raschig rings, Pall rings, saddles, structured packing devices, ceramic foams, reticulated polymer foams, and extrudates, such as alumina, either in bags or loosely packed in the column.

The support comprises a catalyst effective to catalyze the isomerization. Examples of suitable catalysts include, but are not necessarily limited to metals, metal oxides, zeolites, bases, acids, such as phosphoric acid, bauxite, metal hydrides, and organoalkali compounds. Suitable metals include but are not necessarily limited to Ni, Mo, Re, W, and the noble metals. The noble metals include but are not necessarily limited to gold, silver, platinum, palladium, iridium, rhenium, mercury, ruthenium, and osmium. Preferred noble metals are Pt and Pd.

Suitable bases include, but are not necessarily limited to metal hydroxides. Suitable metals and metal oxides include, but are not necessarily limited to those comprising a metal selected from the group consisting of rhenium, noble metals, cobalt, iron, manganese, magnesium, and calcium. A preferred metal oxide is rhenium oxide. Suitable alkali metals include but are not necessarily limited to sodium and potassium. Suitable alkali metal promoted aluminas include, but are not necessarily limited to potassium carbonate promoted aluminas. Other suitable isomerization catalysts are disclosed in the publications "Review of Olefin Isomerization", H. N. Dunning, Industrial and Engineering Chemistry, 45, 551-564 (1953) and "Base-Catalyzed Reactions of Hydrocarbons and Related Compounds", edited by H. Pines and W. M. Stalich, Academic Press, 1977, pp. 25-51, incorporated herein by reference. Preferred isomerization catalysts include, but are not necessarily limited to those comprising $K_2CO_3$, Pt, Pd, or Ni, and combinations thereof. These preferred isomerization catalysts preferably are supported on $SiO_2$ or $Al_2O_3$ and ferrierite or other shape selective zeolites. See U.S. Pat. Nos. 4,727,203; 4,749,819; 4,996,386; 4,895,997; and 5,043,520, each incorporated herein by reference.

If the catalyst must be activated by hydrogen, as generally is true of the noble metal catalysts, or if dienes are present in the feed, hydrogen is fed to the column at an "effective hydrogen flow rate." The "effective hydrogen flow rate" is (a) sufficiently high to support any diene hydrogenation and sufficient to replace hydrogen lost from the catalyst, but (b) sufficiently below the level required to hydrogenate alkenes and to prevent flooding of the column. The isomerization reaction proceeds at a rate of approximately 100 times faster than hydrogenation of the alkenes, so the removal of the reactants from the reaction zones prevents loss of alkenes. Unused hydrogen may be withdrawn from the condenser and recycled as a gas stream, as necessary.

The mixed alkene stream is high in the 1-alkene and homologous alkenes isomerizable to the 1-alkene. Alkanes present in the mixed alkane stream contribute to the vapor loading in the column. High concentrations of dienes in the mixed alkene stream are not desired as they may delay the isomerization reaction. A practical limit to diene content is established by the distillation column bed size and the reaction time available for the hydrogenation and isomerization reactions. Additionally the dienes can be extracted to practical limits before feeding. Examples of suitable mixed alkene streams include, but are not necessarily limited to mixed $C_4$ streams obtained from pyrolysis gas, mixed olefin feeds obtained from a Fischer Tropsh process, and mixed olefin feeds obtained from ethylene oligomerization processes. Examples of known ethylene oligomerization processes include, but are not necessarily limited to the Aufbau or the Shell Higher Olefins process.

Suitable extraction agents are effective to reduce the size of the distillation column required to perform a given separation at a given set of conditions, i.e. by reducing the height or number of required stages, by reducing the diameter of the distillation column, and preferably by reducing both the number of stages and the diameter of the column.

Where the extraction agent reduces column diameter, the extraction agent preferably is effective to reduce the column diameter required to achieve given separation results by about 10% or more, preferably by about 15% or more, more preferably by about 20% or more. Where the extraction agent reduces the number of stages, preferred extraction agents are effective to reduce the number of stages required to achieve given separation results by about 10% or more, preferably by about 15% or more, most preferably by about 20% or more. Preferred extraction agents achieve both a reduction in required column diameter and a reduction in the number of required stages, preferably in the percentages described. In a most preferred embodiment, both the reduction in column diameter and the reduction in number of stages are about 15% or more, more preferably about 20% or more.

Suitable extraction agents for 1-alkenes include, but are not necessarily limited to amides, alcohols, aldehydes, ketones, alkyl carboxylates, amines, diamines, sulfolanes, and alkyl cyanides. The extraction agents suitably have from about 1 to about 20 carbon atoms, preferably from about 1 to about 18 carbon atoms, more preferably from about 1 to about 14 carbon atoms. Preferred extraction agents are amides, more preferably amides selected from the group consisting of N-methyl-2-pyrrolidone (NMP) and dimethyl formamide (DMF).

Preferred alcohols are selected from the group consisting of MIBC (4-methyl-2-pentanol), n-butanol, isobutanol, and isoamyl alcohol (3-methyl-1-butanol). A preferred aldehyde is furfural. Suitable ketones include but are not necessarily limited to acetophenone, dibutyl ketone (5-nonanone), isophorone, 2-pentanone and MIBK (methyl-isobutyl-ketone). Suitable alkyl carboxylates include, but are not necessarily limited to ethyl isovalerate, n-butyl formate, n-hexyl formate, t-butyl acetate, and n-hexyl acetate. Suitable amines include, but are not necessarily limited to diamylamine. Suitable diamines include but are not necessarily limited to ethylenediamine. Suitable alkyl cyanides include but are not necessarily limited to acetonitrile.

In order to perform the catalytic distillation, the supported isomerization catalyst is packed into the distillation column, preferably at or near the bottom of a distillation column having a number of stages effective to recover a particular 1-alkene. The mixed alkene stream is fed to a distillation column. If hydrogen is to be added, the hydrogen is combined with the mixed alkene stream and the combined stream is fed to the distillation column. The feed may be introduced at any effective location along the distillation column, and preferably is introduced near the bottom of the distillation column. The hydrogen (if present) hydrogenates any diene in the feed. As the mixed alkene stream contacts the catalyst, equilibrium amounts of 1-alkene and homologous molecules are produced at the catalyst. The 1-alkene is substantially immediately distilled off and taken overhead, driving the reaction at the catalyst sites toward the production of 1-alkene.

The overhead stream, comprising 1-alkene and the bulk of the corresponding alkanes is fed to a condenser. A portion of the overhead product is recycled to the distillation column as reflux and the remainder is withdrawn and collected as product. Bottoms may be withdrawn or recycled to the catalytic distillation column for complete conversion. Extraction agent, if used, preferably is added to the distillation column continuously at a stage effective to enhance the separation.

Control over the rate of reaction and distribution of products is achieved by regulating the system pressure. Adjusting the throughput (residence time=liquid hourly space velocity$^{-1}$) provides control over the product distribution and degree of conversion to 1-alkene.

During the catalytic distillation process, the column contains a vapor phase and a liquid phase. Since all of the components are boiling, the temperature of reaction is controlled by the boiling point of the mixture at the system pressure. The heat of reaction creates more boil up, but does not increase the temperature. The reaction has an increased driving force because the reaction products are removed by the distillation, and cannot contribute to a reverse reaction (LeChatelier's Principle).

The boiling point of the reaction mixture present at the given pressure determines the temperature in the relevant portion of the distillation column. The temperature in the lower portions of the column reflect the boiling point of the fraction of reaction mixture present in that part of the column, which is higher than the boiling point of the overhead. At constant pressure, a change in the temperature of the system indicates a change in the composition of the reaction mixture present in the column. If the pressure is changed, the temperature changes. Hence, the temperature in the reaction zone is controlled by changing the pressure. When the pressure is increased, the temperature in the system increases. When the pressure is decreased, the temperature in the system decreases.

Preferred temperatures and pressures will vary with the particular 1-alkene being recovered. Preferred pressures and temperatures are those at which the best equilibrium is reached for both isomerization and distillation. The temperature and pressure are effective to recover the 1-alkene and to leave a sufficient amount of liquid to perform the isomerization. The temperature is sufficiently low to avoid destruction of the 1-alkene, and to avoid recovering a significant quantity, preferably any, homologous isomers of the 1-alkene in the distillation overhead. If the temperature is not sufficiently high to recover the 1-alkene, then the pressure is reduced. The pressure may be reduced to the freezing point of the mixed alkenes, or (if alkane is present) the combination of mixed alkenes and alkane, as long as it is possible to boil the 1-alkene.

The temperature in the reaction zone may be as low as the lower level of catalytic activity, which generally is about 20° C. (or room temperature); however, at lower temperatures a vacuum may be necessary to recover the 1-alkene. Suitable reaction zone temperatures where an extraction agent is not present are greater than 0° C. (32° F.), preferably from about 20° C. to the critical temperature of the 1-alkene. Where an extraction agent is present, suitable reaction zone temperatures are from about 0° C. to the critical point of the extraction agent/1-alkene mixture, preferably from about 20° C. to the critical point of the extraction agent/1-alkene mixture.

Condenser temperatures will vary with the 1-alkene, and theoretically may vary from −81° C. to about 254° C. (about −115° F. to about 490° F.) and reboiler temperatures may vary from about −76° C. to about 263° C. (about −105° F. to about 504° F.). The corresponding operating pressures are from about 0.01 atm to about 25 atm. Preferred pressures for $C_5$-$C_8$ 1-alkenes are from about 1 to about 15 atm, more preferably from about 5 to about 13, and most preferably from about 7 to about 10 atm, respectively. The liquid hourly space velocity generally is from about 0.1/hr to about 10/hr, preferably from about 1/hr to about 5/hr, more preferably from about 1/hr to about 2/hr.

In a most preferred embodiment for producing 1-hexene from 3-hexene: the pressure is about 9 atm; the condenser temperature is about 152° C. (about 306° F.); and the reboiler temperature is about 159° C. (about 318° F.).

In an alternate preferred embodiment for producing 1-hexene: the pressure is about 5 atm; the condenser temperature is about 124° C. (255° F.); the reboiler temperature is about 278° C. (533° F.); and, for every pound of hexenes, about 0.5 pound per hour of NMP is added at a point above the midpoint of the distillation column, preferably at a point located in the upper 25% of the column.

In yet another preferred embodiment for producing 1-hexene: the pressure is about 7 atm; the condenser temperature is about 124° C. (255° F.); the reboiler temperature is about 278° C. (533° F.); and, for every pound of hexenes, about 0.1 pound per hour of DMF is added at a point above the midpoint of the distillation column, preferably at a point located in the upper 25% of the column.

Suitable parameters for catalytic distillation of specific 1-alkenes are shown in the following Table:

| 1-alkene | Condenser Temperature | Reboiler Temperature | Pressure |
|---|---|---|---|
| 1-butene | −81 to 35° C. (−115 to 96° F.) | −76 to 42° C. (−105 to 108° F.) | 0.01 to 4 atm |
| 1-pentene | −55 to 169° C. (−67 to 337° F.) | −49 to 176° C. (−57 to 350° F.) | 0.01 to 25 atm |
| 1-hexene | −30 to 192° C. (−22 to 378° F.) | −26 to 200° C. (−15 to 392° F.) | 0.01 to 18 atm |
| 1-heptene | −6 to 220° C. (21 to 429° F.) | −4 to 227° C. (24 to 439° F.) | 0.01 to 15 atm |
| 1-octene | 14 to 254° C. (58 to 490° F.) | 15 to 263° C. (60 to 504° F.) | 0.01 to 15 atm |

Preferred parameters for catalytic distillation of specific 1-alkenes are shown in the following Table:

| 1-alkene | Condenser Temperature | Reboiler Temperature | Pressure |
|---|---|---|---|
| 1-butene | 13-14° C. (56° F.) | 19-20° C. (67° F.) | 2 atm |
| 1-pentene | 106-107° C. (244° F.) | 125° C. (257° F.) | 10 atm |
| 1-hexene | 152-153° C. (306° F.) | 158-159° C. (318° F.) | 9 atm |
| 1-heptene | 190° C. (374° F.) | 195° C. (383° F.) | 9 atm |
| 1-octene | 208-209° C. (407° F.) | 213-214° C. (417° F.) | 7 atm |

Representative comparable parameters for extractive distillation of 1-hexene when about 0.1 pound per hour of DMF for each pound of hexenes is added to the distillation column are shown in the following Table:

| 1-alkene | Condenser Temperature | Reboiler Temperature | Pressure |
|---|---|---|---|
| 1-hexene | 123-124° C. (255° F.) | 278-279° C. (533° F.) | 7 atm |

Representative comparable parameters for extractive distillation of the 1-hexene when 0.5 pound per hour of NMP is added to the distillation column for each pound of hexenes are shown in the following Table:

| 1-alkene | Condenser Temperature | Reboiler Temperature | Pressure |
|---|---|---|---|
| 1-hexene | 123-124° C. (255° F.) | 278-279° C. (533° F.) | 5 atm |

The distillation column has a sufficient number of stages to complete the separation of the 1-alkene from its homologs and to prevent a significant portion of the homologs from being withdrawn overhead in the distillation overhead. The preferred number of stages varies with the number of carbon atoms in the 1-alkene and with the required product purity.

The application is better understood with reference to the following examples, which are illustrative only:

EXAMPLES

Aspen modeling simulations were used to develop a series of examples to illustrate the concept of using catalytic distillation to produce alpha olefins from internal olefins via isomerization and distillation in a single column. In addition, a series of screening calculations were conducted to evaluate candidate solvents for isomerization with extractive distillation in a single column.

Common Modeling Assumptions

The following assumptions were common to all of the simulations that were conducted:
Simulations were conducted with Aspen Plus 10.2.
Only the available default physical property parameters in Aspen Plus 10.2 were used.
The specific physical property method used for all simulations was the NRTL (Renon)/Redlich-Kwong equation of state with Henry's law (NRTL-RK).
The isomerization reactions reached equilibrium as determined by minimization of the Gibbs free energy using the available default data in Aspen Plus 10.2.
Column diameters were determined in Aspen Plus 10.2 assuming a Glitsch Ballast tray type with 2 passes per tray. All other tray-sizing parameters were the defaults available in Aspen Plus 10.2.
Internal olefin feed to each of the process examples was 1000 lb/hr and was added at the bottom of column into the isomerization portion of the column.
Each simulation was conducted with the goal of achieving an alpha olefin product with a purity of 99 wt % for 1-pentene and 1-hexene, and 95 wt % for 1-heptene and 1-octene.

Example 1

Production of 1-pentene from 2-pentene

The 2-pentene feedstock was assumed to have a composition of 33 wt % cis-2-pentene and 67 wt % trans-2-pentene. The Aspen database contains the following normal boiling points for the relevant components:

Boiling points for pentenes.

| Component | Boiling Points ° F. | ° C. |
|---|---|---|
| 1-pentene | 85.9 | 29.9 |
| cis-2-pentene | 98.5 | 36.9 |
| trans-2-pentene | 97.4 | 36.3 |

The isomerization reaction was assumed to occur at the bottom of the column. The column was assumed to have 150 theoretical stages, a kettle reboiler, and a total condenser. Several cases were evaluated by changing the column operating pressure, which was varied from 0.013 to 25 atm. For each case, the condenser temperature, reboiler temperature, reflux ratio, and column diameter were evaluated. A summary of the modeling cases is provided in the following table.

Modeling cases for 1-pentene CD column.

| Case | Condenser Temperature ° F. | ° C. | Reboiler Temperature ° F. | ° C. | P (atm) | Reflux Ratio | Column Diameter (ft) | Comment |
|---|---|---|---|---|---|---|---|---|
| 1 | −67 | −55 | −57 | −49 | 0.013 | 423 | 53.0 | |
| 2 | −1 | −18 | 10 | −12 | 0.13 | 266 | 21.0 | |
| 3 | 25 | −4 | 36 | 2 | 0.26 | 235 | 16.0 | |
| 4 | 53 | 12 | 64 | 18 | 0.50 | 211 | 12.5 | |
| 5 | 86 | 30 | 97 | 36 | 1 | 191 | 10.2 | |
| 6 | 187 | 86 | 199 | 93 | 5 | 163 | 6.9 | |

-continued

| | | | | | | | | |
|---|---|---|---|---|---|---|---|---|
| 7 | 213 | 101 | 226 | 108 | 7 | 162 | 6.7 | |
| 8 | 235 | 113 | 248 | 120 | 9 | 163 | 6.6 | |
| 9 | 244 | 118 | 257 | 125 | 10 | 165 | 6.5 | Optimal case |
| 10 | 261 | 127 | 266 | 130 | 11 | 166 | 6.5 | Optimal case |
| 11 | 253 | 123 | 274 | 134 | 12 | 168 | 6.6 | |
| 12 | 313 | 156 | 326 | 163 | 20 | 206 | 7.4 | |
| 13 | 337 | 169 | 350 | 177 | 25 | 308 | 9.7 | |

1-pentene critical point

| | | |
|---|---|---|
| Critical temperature | 192 | ° C. |
| | 377 | ° F. |
| Critical pressure | 35 | atm |

In an optimal case (smallest diameter column) for producing 1-pentene, the pressure was 10 atm, the condenser temperature was 118° C. (244° F.), and reboiler temperature was 125° C. (257° F.). This resulted in a column with a diameter of 6.5 ft and a reflux ratio of 165. For this case, the 1000 lb/hr 2-pentene feed resulted in 980 lb/hr of 99 wt % 1-pentene product.

A detailed material balance for this optimal case is shown in the following table. RXFEED is the distillation column feed stream, BOTTOMS is the distillation column bottoms stream, and 1-PENTENE is the product stream which is obtained from the top of the column.

Aspen material balance for 1-pentene optimal case (9).

| | Stream | | |
|---|---|---|---|
| | RXFEED | 1-PENTENE | BOTTOMS |
| Temperature, ° C. (° F.) | 100 (212) | 118 (244) | 125 (257) |
| Pressure, psi | 14.7 | 146.96 | 146.96 |
| Vapor Fraction | 1 | 0 | 0 |
| Mole Flow, lbmol/hr | 14.258 | 14.116 | 0.143 |
| Mass Flow, lb/hr | 1000 | 990 | 10 |
| Volume Flow, cuft/hr | 6862.197 | 34.787 | 0.308 |
| Enthalpy, MMBtu/hr | −0.129 | −0.185 | −0.002 |
| Mass Flow, lb/hr | | | |
| 1-pentene | 0 | 980.123 | 0.525 |
| cis-2-pentene | 333 | 0.065 | 2.396 |
| trans-2-pentene | 667 | 9.812 | 7.079 |
| Mass Fraction | | | |
| 1-pentene | 0 | 0.99 | 0.053 |
| cis-2-pentene | 0.333 | 0 | 0.24 |
| trans-2-pentene | 0.667 | 0.01 | 0.708 |
| Mole Flow, lbmol/hr | | | |
| 1-pentene | 0 | 13.975 | 0.007 |
| cis-2-pentene | 4.748 | 0.001 | 0.034 |
| trans-2-pentene | 9.51 | 0.14 | 0.101 |
| Mole Fraction | | | |
| 1-pentene | 0 | 0.99 | 0.053 |
| cis-2-pentene | 0.333 | 0 | 0.24 |
| trans-2-pentene | 0.667 | 0.01 | 0.708 |
| Liquid Volume 16° C. (60° F.), cuft/hr | | | |
| 1-pentene | 0 | 24.381 | 0.013 |
| cis-2-pentene | 8.094 | 0.002 | 0.058 |
| trans-2-pentene | 16.396 | 0.241 | 0.174 |
| Liquid Fraction 16° C. (60° F.) | | | |
| 1-pentene | 0 | 0.99 | 0.053 |
| cis-2-pentene | 0.331 | 0 | 0.237 |
| trans-2-pentene | 0.669 | 0.01 | 0.709 |

Example 2

Production of 1-hexene from 3-hexene

The 3-hexene feedstock was assumed to have a composition of 33 wt % cis-3-hexene and 67 wt % trans-3-hexene. The Aspen database contains the following normal boiling points for the relevant components:

| | Boiling Points | |
|---|---|---|
| Component | ° F. | ° C. |
| 1-hexene | 146.3 | 63.5 |
| cis-2-hexene | 156.0 | 68.9 |
| trans-2-hexene | 154.2 | 67.9 |
| cis-3-hexene | 151.6 | 66.5 |
| trans-3-hexene | 152.8 | 67.1 |

The isomerization reaction was assumed to occur at the bottom of the column. The column was assumed to have 150 theoretical stages, a kettle reboiler, and a total condenser. Several cases were evaluated by changing the column operating pressure, which was varied from 0.013 atm to 30 atm. For each case, the condenser temperature, reboiler temperature, reflux ratio, and column diameter were evaluated. A summary of the modeling cases is provided in the following table.

Modeling cases for 1-hexene CD column.

| | Condenser Temperature | | Reboiler Temperature | | P | Reflux | Column Diameter | Com- |
|---|---|---|---|---|---|---|---|---|
| Case | ° F. | ° C. | ° F. | ° C. | (atm) | Ratio | (ft) | ment |
| 1 | −22 | −30 | −15 | −26 | 0.013 | 2535 | 127.0 | |
| 2 | 52 | 11 | 59 | 15 | 0.13 | 1570 | 50.2 | |
| 3 | 80 | 27 | 88 | 31 | 0.26 | 1352 | 37.9 | |
| 4 | 110 | 43 | 118 | 48 | 0.50 | 1169 | 29.2 | |
| 5 | 146 | 63 | 155 | 68 | 1.00 | 995 | 23.3 | |
| 6 | 216 | 102 | 225 | 107 | 3 | 766 | 16.6 | |
| 7 | 255 | 124 | 265 | 130 | 5 | 687 | 14.4 | |
| 8 | 270 | 132 | 281 | 138 | 6 | 666 | 13.8 | |
| 9 | 283 | 139 | 295 | 146 | 7 | 651 | 13.5 | |
| 10 | 295 | 146 | 307 | 153 | 8 | 644 | 13.3 | |
| 11 | 306 | 152 | 318 | 159 | 9 | 643 | 13.2 | Optimal case |
| 12 | 316 | 158 | 328 | 165 | 10 | 647 | 13.2 | Optimal case |
| 13 | 335 | 168 | 347 | 175 | 12 | 680 | 13.6 | |
| 14 | 351 | 177 | 363 | 184 | 14 | 770 | 14.7 | |
| 15 | 358 | 181 | 371 | 188 | 15 | 864 | 15.8 | |
| 16 | 378 | 192 | 392 | 200 | 18 | 2320 | 30.2 | |
| 17 | 390 | 199 | 404 | 207 | 20 | — | — | Model did not converge |
| 18 | 451 | 233 | 458 | 237 | 30 | — | — | Model did not converge |

1-hexene critical point

| | | |
|---|---|---|
| Critical temperature | 231 | ° C. |
| | 447 | ° F. |
| Critical pressure | 31.6 | atm |

In an optimal case (smallest diameter column) for producing 1-hexene from 3-hexene, the pressure was 9 atm, the condenser temperature was 152° C. (306° F.), and the reboiler temperature was 159° C. (318° F.). This resulted in a column with a diameter of 13.2 ft and a reflux ratio of 643. For this case, the 1000 lb/hr 3-hexene feed resulted in 980 lb/hr of 99 wt % 1-hexene product. A detailed material balance for this optimal case is shown in the following table. RXFEED is the distillation column feed stream, BOTTOMS is the distillation column bottoms streams, and 1-HEXENE is the product stream which is obtained from the top of the column.

Aspen material balance for 1-hexene optimal case (11).

| | Stream | | |
|---|---|---|---|
| | 1-HEXENE | BOTTOMS | RXFEED |
| Temperature, ° C. (° F.) | 152 (306) | 159 (318) | 100 (212) |
| Pressure, psi | 132.3 | 132.3 | 14.7 |
| Vapor Fraction | 0 | 0 | 1 |
| Mole Flow, lbmol/hr | 11.763 | 0.119 | 11.882 |
| Mass Flow, lb/hr | 990 | 10 | 1000 |
| Volume Flow, cuft/hr | 30.17 | 0.313 | 5673.407 |
| Enthalpy, MMBtu/hr | −0.233 | −0.003 | −0.213 |
| Mass Flow, lb/hr | | | |
| 1-hexene | 980.12 | 0.161 | 0 |
| cis-2-hexene | 0.149 | 4.218 | 0 |
| trans-2-hexene | 0.11 | 3.276 | 0 |
| cis-3-hexene | 2.02 | 0.462 | 333 |
| trans-3-hexene | 7.601 | 1.883 | 667 |
| Mass Fraction | | | |
| 1-hexene | 0.99 | 0.016 | 0 |
| cis-2-hexene | 0 | 0.422 | 0 |
| trans-2-hexene | 0 | 0.328 | 0 |
| cis-3-hexene | 0.002 | 0.046 | 0.333 |
| trans-3-hexene | 0.008 | 0.188 | 0.667 |
| Mole Flow, lbmol/hr | | | |
| 1-hexene | 11.646 | 0.002 | 0 |
| cis-2-hexene | 0.002 | 0.05 | 0 |
| trans-2-hexene | 0.001 | 0.039 | 0 |
| cis-3-hexene | 0.024 | 0.005 | 3.957 |
| trans-3-hexene | 0.09 | 0.022 | 7.925 |
| Mole Fraction | | | |
| 1-hexene | 0.99 | 0.016 | 0 |
| cis-2-hexene | 0 | 0.422 | 0 |
| trans-2-hexene | 0 | 0.328 | 0 |
| cis-3-hexene | 0.002 | 0.046 | 0.333 |
| trans-3-hexene | 0.008 | 0.188 | 0.667 |
| Liquid Volume 16° C. (60° F.), cuft/hr | | | |
| 1-hexene | 23.22 | 0.004 | 0 |
| cis-2-hexene | 0.003 | 0.098 | 0 |
| trans-2-hexene | 0.003 | 0.077 | 0 |
| cis-3-hexene | 0.047 | 0.011 | 7.811 |
| trans-3-hexene | 0.179 | 0.044 | 15.705 |
| Liquid Fraction 16° C. (60° F.) | | | |
| 1-hexene | 0.99 | 0.016 | 0 |
| cis-2-hexene | 0 | 0.418 | 0 |
| trans-2-hexene | 0 | 0.329 | 0 |
| cis-3-hexene | 0.002 | 0.046 | 0.332 |
| trans-3-hexene | 0.008 | 0.19 | 0.668 |

Example 3

Production of 1-heptene from 2-heptene

The 2-heptene feedstock was assumed to have a composition of 33 wt % cis-2-heptene and 67 wt % trans-2-heptene. The Aspen database contains the following normal boiling points for the relevant components:

Boiling points for heptenes.

| | Boiling Points | |
|---|---|---|
| Component | ° F. | ° C. |
| 1-heptene | 200.5 | 93.6 |
| Cis-2-heptene | 209.1 | 98.4 |
| trans-2-heptene | 208.3 | 97.9 |
| Cis-3-heptene | 204.4 | 95.8 |
| trans-3-heptene | 204.2 | 95.7 |

The isomerization reaction was assumed to occur at the bottom of the column. The column was assumed to have 150 theoretical stages, a kettle reboiler, and a total condenser. Several cases were evaluated by changing the column operating pressure, which was varied from 0.013 atm to 20 atm. For each case, the condenser temperature, reboiler temperature, reflux ratio, and column diameter were evaluated. A summary of the modeling cases is provided in the following table.

Modeling cases for 1-heptene CD column.

| Case | Condenser Temperature | | Reboiler Temperature | | P (atm) | Reflux Ratio | Column Diameter (ft) | Comment |
|---|---|---|---|---|---|---|---|---|
| | ° F. | ° C. | ° F. | ° C. | | | | |
| 1 | 21 | −6 | 24 | −4 | 0.01 | 3132 | 139.3 | |
| 2 | 99 | 37 | 103 | 39 | 0.13 | 1674 | 50.7 | |
| 3 | 162 | 72 | 167 | 75 | 0.50 | 1416 | 31.6 | |
| 4 | 200 | 93 | 206 | 97 | 1 | 1452 | 28.2 | |
| 5 | 319 | 159 | 326 | 163 | 5 | 1186 | 19.4 | |
| 6 | 363 | 184 | 371 | 188 | 8 | 1027 | 17.0 | |
| 7 | 374 | 190 | 383 | 195 | 9 | 1023 | 16.7 | Optimal case |
| 8 | 385 | 196 | 394 | 201 | 10 | 1043 | 17.0 | |
| 9 | 429 | 221 | 439 | 226 | 15 | 2046 | 26.4 | |
| 10 | 463 | 239 | 473 | 245 | 20 | — | — | Model did not converge |

1-heptene critical point

| Critical temperature | 264 | ° C. |
|---|---|---|
| | 508 | ° F. |
| Critical pressure | 28.8 | atm |

In an optimal case (smallest diameter column) for producing 1-heptene from 2-heptene, the pressure was 9 atm, the condenser temperature was 190° C. (374° F.), and the reboiler temperature was 195° C. (383° F.). This resulted in a column with a diameter of 16.7 ft and a reflux ratio of 1023. For this case, the 1000 lb/hr 2-heptene feed resulted in 940 lb/hr of 95 wt % 1-heptene product. A detailed material balance for this optimal case is shown in the following table. RXFEED is the distillation column feed stream, BOTTOMS is the distillation column bottoms stream, and 1-HEPTENE is the product stream, which is obtained from the top of the column.

| Aspen material balance for 1-heptene optimal case (7). | | | |
|---|---|---|---|
| | Stream | | |
| | RXFEED | 1-HEPTENE | BOTTOMS |
| Temperature, °C. (°F.) | 100 (212) | 190 (375) | 194 (383) |
| Pressure, psi | 14.7 | 132.26 | 132.26 |
| Vapor Fraction | 1 | 0 | 0 |
| Mole Flow, lbmol/hr | 10.185 | 10.083 | 0.102 |
| Mass Flow, lb/hr | 1000 | 990 | 10 |
| Volume Flow, cuft/hr | 4816.4 | 30.123 | 0.308 |
| Enthalpy, MMBtu/hr | −0.265 | −0.248 | −0.003 |
| Mass Flow, lb/hr | | | |
| 1-heptene | 0 | 940.414 | 0.25 |
| cis-2-heptene | 333 | 0.001 | 1.005 |
| trans-2-heptene | 667 | 0.636 | 4.097 |
| cis-3-heptene | 0 | 0.984 | 0.945 |
| trans-3-heptene | 0 | 47.966 | 3.702 |
| Mass Fraction | | | |
| 1-heptene | 0 | 0.95 | 0.025 |
| cis-2-heptene | 0.333 | 0 | 0.1 |
| trans-2-heptene | 0.667 | 0.001 | 0.41 |
| cis-3-heptene | 0 | 0.001 | 0.095 |
| trans-3-heptene | 0 | 0.048 | 0.37 |
| Mole Flow, lbmol/hr | | | |
| 1-heptene | 0 | 9.578 | 0.003 |
| cis-2-heptene | 3.391 | 0 | 0.01 |
| trans-2-heptene | 6.793 | 0.006 | 0.042 |
| cis-3-heptene | 0 | 0.01 | 0.01 |
| trans-3-heptene | 0 | 0.489 | 0.038 |
| Mole Fraction | | | |
| 1-heptene | 0 | 0.95 | 0.025 |
| cis-2-heptene | 0.333 | 0 | 0.1 |
| trans-2-heptene | 0.667 | 0.001 | 0.41 |
| cis-3-heptene | 0 | 0.001 | 0.095 |
| trans-3-heptene | 0 | 0.048 | 0.37 |
| Liquid Volume 16°C. (60°F.), cuft/hr | | | |
| 1-heptene | 0 | 21.53 | 0.006 |
| cis-2-heptene | 7.59 | 0 | 0.023 |
| trans-2-heptene | 15.331 | 0.015 | 0.094 |
| cis-3-heptene | 0 | 0.023 | 0.022 |
| trans-3-heptene | 0 | 1.107 | 0.085 |
| Liquid Fraction 16°C. (60°F.) | | | |
| 1-heptene | 0 | 0.95 | 0.025 |
| cis-2-heptene | 0.331 | 0 | 0.1 |
| trans-2-heptene | 0.669 | 0.001 | 0.41 |
| cis-3-heptene | 0 | 0.001 | 0.094 |
| trans-3-heptene | 0 | 0.049 | 0.372 |

Example 4

Production of 1-octene from 2-octene

The 2-octene feedstock was assumed to have a composition of 33 wt % cis-2-octene and 67 wt % trans-2-octene. The Aspen database contains the following normal boiling points for the relevant components.

| Boiling points for octenes. | | |
|---|---|---|
| | Boiling Points | |
| Component | °F. | °C. |
| 1-octene | 250.3 | 121.3 |
| cis-2-octene | 258.2 | 125.7 |
| trans-2-octene | 257.0 | 125.0 |
| cis-3-octene | 253.2 | 122.9 |
| trans-3-octene | 253.9 | 123.3 |
| cis-4-octene | 252.6 | 122.6 |
| trans-4-octene | 252.2 | 122.3 |

The isomerization reaction was assumed to occur at the bottom of the column. The column was assumed to have 150 theoretical stages, a kettle reboiler, and a total condenser. Several cases were evaluated by changing the column operating pressure, which was varied from 0.013 atm to 15 atm. For each case, the condenser temperature, reboiler temperature, reflux ratio, and column diameter were evaluated. A summary of the modeling cases is provided in the following table.

| Modeling cases for 1-octene CD column. | | | | | | | |
|---|---|---|---|---|---|---|---|
| | Condenser Temperature | | Reboiler Temperature | | P | Reflux | Column Diameter | Comment |
| Case | °F. | °C. | °F. | °C. | (atm) | Ratio | (ft) | |
| 1 | 58 | 14 | 60 | 16 | 0.013 | — | — | Model did not converge |
| 2 | 142 | 61 | 144 | 62 | 0.13 | — | — | Model did not converge |
| 3 | 250 | 121 | 254 | 123 | 1 | — | — | Model did not converge |
| 4 | 375 | 191 | 383 | 195 | 5 | 1160 | 19.4 | |
| 5 | 392 | 200 | 401 | 205 | 6 | 1106 | 18.5 | |
| 6 | 407 | 208 | 417 | 214 | 7 | 1089 | 18.0 | Optimal case |
| 7 | 421 | 216 | 431 | 222 | 8 | 1090 | 18.0 | Optimal case |
| 8 | 433 | 223 | 444 | 229 | 9 | 1119 | 18.2 | |
| 9 | 444 | 229 | 456 | 236 | 10 | 1173 | 18.8 | |
| 10 | 490 | 254 | 504 | 262 | 15 | 2620 | 32.6 | |

1-octene critical point

| | | |
|---|---|---|
| Critical temperature | 293 | °C. |
| | 561 | °F. |
| Critical pressure | 26.4 | Atm |

In an optimal case (smallest diameter column) for producing 1-octene from 2-octene, the pressure was 7 atm, the condenser temperature was 208°C. (407°F.), and the reboiler temperature was 214°C. (417°F.). This resulted in a column with a diameter of 18.0 ft and a reflux ratio of 1089. For this case, the 1000 lb/hr 2-octene feed resulted in 940 lb/hr of 95 wt % 1-octene product. A detailed material balance is shown in the following table. RXFEED is the distillation column feed stream, BOTTOMS is the distillation column bottoms stream, and 1-OCTENE is the product stream which is obtained from the top of the column.

Aspen material balance for 1-octene optimal case (6).

| | Stream | | |
|---|---|---|---|
| | RXFEED | 1-OCTENE | BOTTOMS |
| Temperature, °C. (°F.) | 100 (212) | 209 (407) | 214 (417) |
| Pressure, psi | 14.7 | 102.87 | 102.87 |
| Vapor Fraction | 0 | 0 | 0 |
| Mole Flow, lbmol/hr | 8.911 | 8.822 | 0.089 |
| Mass Flow, lb/hr | 1000 | 990 | 10 |
| Volume Flow, cuft/hr | 25.35 | 29.596 | 0.31 |
| Enthalpy, MMBtu/hr | −0.441 | −0.272 | −0.003 |
| Mass Flow, lb/hr | | | |
| 1-octene | 0 | 940.414 | 0.216 |
| cis-2-octene | 333 | 0.022 | 0.693 |
| trans-2-octene | 667 | 0.008 | 3.127 |
| cis-3-octene | 0 | 17.335 | 0.794 |
| trans-3-octene | 0 | 0.297 | 3.228 |
| cis-4-octene | 0 | 31.291 | 0.396 |
| trans-4-octene | 0 | 0.633 | 1.546 |
| Mass Fraction | | | |
| 1-octene | 0 | 0.95 | 0.022 |
| cis-2-octene | 0.333 | 0 | 0.069 |
| trans-2-octene | 0.667 | 0 | 0.313 |
| cis-3-octene | 0 | 0.018 | 0.079 |
| trans-3-octene | 0 | 0 | 0.323 |
| cis-4-octene | 0 | 0.032 | 0.04 |
| trans-4-octene | 0 | 0.001 | 0.155 |
| Mole Flow, lbmol/hr | | | |
| 1-octene | 0 | 8.38 | 0.002 |
| cis-2-octene | 2.968 | 0 | 0.006 |
| trans-2-octene | 5.944 | 0 | 0.028 |
| cis-3-octene | 0 | 0.154 | 0.007 |
| trans-3-octene | 0 | 0.003 | 0.029 |
| cis-4-octene | 0 | 0.279 | 0.004 |
| trans-4-octene | 0 | 0.006 | 0.014 |
| Mole Fraction | | | |
| 1-octene | 0 | 0.95 | 0.022 |
| cis-2-octene | 0.333 | 0 | 0.069 |
| trans-2-octene | 0.667 | 0 | 0.313 |
| cis-3-octene | 0 | 0.018 | 0.079 |
| trans-3-octene | 0 | 0 | 0.323 |
| cis-4-octene | 0 | 0.032 | 0.04 |
| trans-4-octene | 0 | 0.001 | 0.155 |
| Liquid Volume 16°C. (60°F.), cuft/hr | | | |
| 1-octene | 0 | 20.996 | 0.005 |
| cis-2-octene | 7.408 | 0 | 0.015 |
| trans-2-octene | 14.79 | 0 | 0.069 |
| cis-3-octene | 0 | 0.387 | 0.018 |
| trans-3-octene | 0 | 0.007 | 0.073 |
| cis-4-octene | 0 | 0.699 | 0.009 |
| trans-4-octene | 0 | 0.014 | 0.035 |
| Liquid Fraction 16°C. (60°F.) | | | |
| 1-octene | 0 | 0.95 | 0.022 |
| cis-2-octene | 0.334 | 0 | 0.069 |
| trans-2-octene | 0.666 | 0 | 0.31 |
| cis-3-octene | 0 | 0.018 | 0.079 |
| trans-3-octene | 0 | 0 | 0.325 |
| cis-4-octene | 0 | 0.032 | 0.04 |
| trans-4-octene | 0 | 0.001 | 0.156 |

Example 5

Screening of Solvents to Improve 1-hexene Separation via Extractive Distillation Aspen Plus simulations were used to screen a series of solvents to assess their potential to improve the separation of 1-hexene from 2- and 3-hexene in order to minimize the size of the catalytic distillation column. The list of potential solvents was developed from a short literature search in SciFinder 2002 and a short search of publicly available information on the Internet. A total of 26 solvents were screened.

Solvent screening for extractive distillation.

| Solvent | Synonym | Formula | CAS # | Boiling Point °F. | °C. |
|---|---|---|---|---|---|
| N,N-DIMETHYLFORMAMIDE | DMF | $C_3H_7NO$ | 68-12-2 | 305 | 152 |
| ACETONITRILE | | $C_2H_3N$ | 75-05-8 | 179 | 82 |
| N-HEXYL-FORMATE | | $C_7H_{14}O_2$ | 629-33-4 | 312 | 156 |
| N-METHYL-2-PYRROLIDONE | NMP | $C_5H_9NO$ | 872-50-4 | 400 | 204 |
| METHANOL | | $CH_4O$ | 67-56-1 | 148 | 64 |
| ETHANOL | | $C_2H_6O$ | 64-17-5 | 173 | 78 |
| 1-PROPANOL | | $C_3H_8O$ | 71-23-8 | 207 | 97 |
| N-BUTANOL | | $C_4H_{10}O$ | 71-36-3 | 244 | 118 |
| ETHYL-ISOVALERATE | | $C_7H_{14}O_2$ | 108-94-5 | 274 | 134 |
| METHYL-TERT-BUTYL-ETHER | MTBE | $C_5H_{12}O$ | 1634-04-4 | 131 | 55 |
| ISOBUTANOL | | $C_4H_{10}O$ | 78-83-1 | 226 | 108 |
| ISOPHORONE | | $C_9H_{14}O$ | 78-59-1 | 419 | 215 |
| N-BUTYL-FORMATE | | $C_5H_{10}O_2$ | 592-84-7 | 223 | 106 |
| DIAMYLAMINE | | $C_{10}H_{23}N$ | 2050-92-2 | 397 | 203 |
| ETHYLENEDIAMINE | | $C_2H_8N_2$ | 107-15-3 | 243 | 117 |
| FURFURAL | | $C_5H_4O_2$ | 98-01-1 | 323 | 162 |
| SULFOLANE | | $C_4H_8O_2S$ | 126-33-0 | 549 | 287 |
| 4-METHYL-2-PENTANOL | MIBC | $C_6H_{14}O$ | 108-11-2 | 269 | 132 |
| METHYL-PROPIONATE | | $C_4H_8O_2$ | 554-12-1 | 175 | 79 |
| N-HEXYL-ACETATE | | $C_8H_{16}O_2$ | 142-92-7 | 341 | 172 |
| METHYL-PHENYL-KETONE | Acetophenone | $C_8H_8O$ | 98-86-2 | 396 | 202 |

-continued

Solvent screening for extractive distillation.

| Solvent | Synonym | Formula | CAS # | Boiling Point °F. | Boiling Point °C. |
|---|---|---|---|---|---|
| 3-METHYL-1-BUTANOL | Isoamyl alcohol | $C_5H_{12}O$ | 123-51-3 | 268 | 131 |
| METHYL-N-PROPYL-KETONE | 2-pentanone | $C_5H_{10}O$ | 107-87-9 | 216 | 102 |
| TERT-BUTYL-ACETATE | | $C_6H_{12}O_2$ | 540-88-5 | 204 | 96 |
| 5-NONANONE | Dibutyl ketone | $C_9H_{18}O$ | 502-56-7 | 371 | 188 |
| METHYL-ISOBUTYL-KETONE | MIBK | $C_6H_{12}O$ | 108-10-1 | 241 | 116 |

As discussed above, only the default data in Aspen were used for the calculations. This is an important assumption as no attempt was made to verify the quality of the interaction parameters (if present) for the components in the distillation column. In many cases, interaction parameters were not available and the systems were modeled as ideal. Different amounts of solvent and different operating conditions for the column were evaluated. All possible combinations were not considered, so this effort did not result in a true optimization. It was only intended as an example to demonstrate the possibility of an improvement in the separation of 1-hexene from 2- and 3-hexene.

The following specific assumptions were used to screen the solvents for potential to improve the separation of 1-hexene from 2- and 3-hexene: (1) column had 150 stages, (2) the isomerization reaction occurred in the bottom of the column, (3) the solvent was added to stage #10 (from the top) unless otherwise noted, (4) the extraction solvent did not affect the isomerization reaction equilibrium, and (5) the target product was 99 wt % 1-hexene. Many cases were evaluated and the results are summarized in the following table. The base case for this example was assumed to be a column operating at 1 atm pressure.

Screening of extractive distillation solvents for 1-hexene production.

| Solvent | Solvent Flow (lb/hr) | Pressure (atm) | Reflux Ratio | Column Diameter (ft) | Comment |
|---|---|---|---|---|---|
| NMP | 500 | 5 | 455 | 11.4 | |
| NMP | 500 | 7 | 505 | 11.7 | |
| DMF | 100 | 7 | 518 | 11.8 | |
| DMF | 100 | 8 | 526 | 11.9 | |
| DMF | 100 | 6 | 518 | 12 | |
| NMP | 500 | 9 | 585 | 12.5 | |
| DMF | 200 | 6 | 575 | 12.7 | |
| DMF | 200 | 7 | 598 | 12.8 | |
| DMF | 200 | 5 | 563 | 12.9 | |
| None | 0 | 10 | 644 | 13.2 | |
| DMF | 200 | 4 | 560 | 13.3 | |
| Furfural | 500 | 4 | 602 | 13.8 | |
| Furfural | 500 | 4.5 | 617 | 13.8 | |
| Furfural | 500 | 5 | 636 | 13.8 | |
| Furfural | 600 | 5 | 686 | 14.1 | |
| Furfural | 500 | 7 | 690 | 14.1 | |
| Furfural | 500 | 3 | 581 | 14.2 | |
| Furfural | 550 | 5 | 661 | 14.4 | |
| None | 0 | 5 | 687 | 14.5 | |
| Furfural | 500 | 2 | 582 | 15.2 | |
| DMF | 500 | 5 | 766 | 15.3 | |
| DMF | 500 | 5 | 766 | 15.4 | |
| DMF | 500 | 3 | 685 | 15.6 | |
| Furfural | 800 | 5 | 788 | 15.6 | |
| None | 0 | 15 | 851 | 15.7 | |
| Ethyl isovalerate | 500 | 5 | 812 | 15.9 | |
| DMF | 500 | 2 | 667 | 16.4 | |
| NMP | 900 | 1 | 546 | 16.7 | Solvent on stage #10 |
| NMP | 900 | 1 | 546 | 16.7 | Solvent on stage #50 |
| NMP | 900 | 1 | 546 | 16.7 | Solvent on stage #140 |
| NMP | 800 | 1 | 560 | 16.9 | |
| NMP | 700 | 1 | 578 | 17.3 | |
| Furfural | 500 | 1 | 635 | 18.1 | |
| Furfural | 500 | 1 | 635 | 18.1 | |
| NMP | 500 | 1 | 630 | 18.1 | |
| NMP | 500 | 1 | 630 | 18.1 | |
| Furfural | 400 | 1 | 646 | 18.3 | |
| n-hexyl acetate | 500 | 1 | 659 | 18.5 | |
| Acetophenone | 500 | 1 | 661 | 18.7 | |
| dibutyl ketone | 500 | 1 | 670 | 18.7 | |
| DMF | 300 | 1 | 675 | 18.7 | |
| DMF | 400 | 1 | 677 | 18.7 | |
| Furfural | 300 | 1 | 669 | 18.7 | |
| n-hexyl formate | 500 | 1 | 669 | 18.7 | |
| NMP | 400 | 1 | 670 | 18.7 | |
| DMF | 500 | 1 | 687 | 18.9 | |
| DMF | 500 | 1 | 687 | 18.9 | |
| n-hexyl acetate | 400 | 1 | 687 | 18.9 | |
| DMF | 500 | 1 | 688 | 19 | |
| DMF | 200 | 1 | 694 | 19.1 | |
| Diamylamine | 500 | 1 | 711 | 19.3 | |
| Isophorone | 500 | 1 | 710 | 19.3 | |
| DMF | 500 | 10 | 1307 | 19.9 | |
| DMF | 100 | 1 | 764 | 20.1 | |
| DMF | 100 | 1 | 764 | 20.1 | |
| Ethyl isovalerate | 500 | 1 | 778 | 20.3 | |
| MIBC | 300 | 1 | 779 | 20.3 | |
| NMP | 200 | 1 | 796 | 20.5 | |
| MIBC | 400 | 1 | 810 | 20.7 | |
| Furfural | 100 | 1 | 814 | 20.8 | |
| Sulfolane | 400 | 1 | 828 | 21 | |
| n-butanol | 100 | 1 | 843 | 21.2 | |
| n-hexyl formate | 100 | 1 | 842 | 21.2 | |
| Isoamyl alcohol | 500 | 1 | 900 | 22 | |
| NMP | 100 | 1 | 900 | 22 | |
| n-butyl formate | 50 | 1 | 913 | 22.1 | |
| Diamylamine | 100 | 1 | 947 | 22.6 | |
| n-butyl formate | 100 | 1 | 949 | 22.6 | |
| None | 0 | 1 | 995 | 23.3 | Base Case |
| None | 0 | 1 | 995 | 23.3 | |
| Ethyl isovalerate | 500 | 0.5 | 849 | 24.5 | |
| MIBK | 500 | 1 | 1159 | 25.3 | |
| n-butanol | 500 | 1 | 1346 | 27.5 | |
| Ethylenediamine | 500 | 1 | 1479 | 29 | |
| n-butyl formate | 500 | 1 | 1583 | 30.2 | |
| t-butyl acetate | 400 | 1 | 1934 | 33.8 | |

-continued

Screening of extractive distillation
solvents for 1-hexene production.

| Solvent | Solvent Flow (lb/hr) | Pressure (atm) | Reflux Ratio | Column Diameter (ft) | Comment |
|---|---|---|---|---|---|
| Isobutanol | 500 | 1 | 1943 | 33.9 | |
| 2-pentanone | 500 | 1 | 2035 | 34.9 | |
| DMF | 500 | 0.1 | 1071 | 44 | |
| Ethyl isovalerate | 500 | 0.1 | 1163 | 46.1 | |
| Acetonitrile | 100 | 1 | 3576 | 48.7 | |
| Acetonitrile | 500 | 1 | — | — | No convergence |
| DMF | 1000 | 1 | — | — | No convergence |
| MIBC | 500 | 1 | — | — | No convergence |
| NMP | 1000 | 1 | — | — | No convergence |
| NMP | 900 | 5 | — | — | No convergence |
| Methyl propionate | 500 | 1 | >6000 | >50 | |

These results show that the use of an extractive distillation solvent has the potential to decrease the column diameter. Many of the solvents resulted in some improvement in the 1-hexene separation. In some cases, it was not possible to get the simulations to converge. The most significant improvements were with N-methyl-2-pyrrolidone (NMP) and N,N-dimethylformamide (DMF). Under certain conditions, the use of NMP or DMF could reduce the column diameter by up to ~20% for the same operating conditions. Two specific examples using NMP and DMF are described below. Similar results are expected for $C_4$ to $C_8$ alkenes.

Example 6

Production of 1-hexene from 3-hexene using NMP to Improve 1-hexene Separation via Extractive Distillation The 3-hexene feedstock was assumed to have a composition of 33 wt % cis-3-hexene and 67 wt % trans-3-hexene. The normal boiling points for 1-, 2-, and 3-hexene are listed in Example 2. The normal boiling for NMP, the extraction solvent in this example, is 204° C. (400° F.). The isomerization reaction was assumed to occur at the bottom of the column. The column was assumed to have 150 theoretical stages, a kettle reboiler, and a total condenser. The operating conditions for the column consisted of a pressure of 5 atm, condenser temperature of 124° C. (255° F.), and reboiler temperature of 279° C. (533° F.). In addition, 500 lb/hr of NMP was added to the 10th theoretical stage of the column (near the top). This resulted in a column with a diameter of 11.4 ft and a reflux ratio of 455. For this case, the 1000 lb/hr 3-hexene feed resulted in 980 lb/hr of 99 wt % 1-hexene product. The column bottoms contained 98 wt % NMP, which can be recycled back to the column. A detailed material balance is shown in the following table. RXFEED is the distillation column feed stream, SOLVENT is the NMP extractive distillation solvent stream, BOTTOMS is the distillation column bottoms stream, and 1-HEXENE is the product stream, which is obtained from the top of the column.

Aspen material balance for 1-hexene via extractive
isomerization/extractive distillation with NMP.

| | Stream | | | |
|---|---|---|---|---|
| | 1-HEXENE | BOTTOMS | RXFEED | SOLVENT |
| Temperature, ° C. (° F.) | 124 (255) | 279 (533) | 100 (212) | 100 (212) |
| Pressure, psi | 73.48 | 73.48 | 14.7 | 14.7 |
| Vapor Fraction | 0 | 0 | 1 | 0 |
| Mole Flow, lbmol/hr | 11.763 | 5.163 | 11.882 | 5.044 |
| Mass Flow, lb/hr | 990 | 510 | 1000 | 500 |
| Volume Flow, cuft/hr | 28.071 | 11.171 | 5673.407 | 8.784 |
| Enthalpy, MMBtu/hr | −0.266 | −0.464 | −0.213 | −0.548 |
| Mass Flow, lb/hr | | | | |
| 1-hexene | 980.02 | 0.337 | 0 | 0 |
| cis-2-hexene | 0.057 | 4.166 | 0 | 0 |
| trans-2-hexene | 0.131 | 3.109 | 0 | 0 |
| cis-3-hexene | 3.913 | 0.607 | 333 | 0 |
| trans-3-hexene | 5.878 | 1.78 | 667 | 0 |
| NMP | 0 | 500 | 0 | 500 |
| Mass Fraction | | | | |
| 1-hexene | 0.99 | 0.001 | 0 | 0 |
| cis-2-hexene | 0 | 0.008 | 0 | 0 |
| trans-2-hexene | 0 | 0.006 | 0 | 0 |
| cis-3-hexene | 0.004 | 0.001 | 0.333 | 0 |
| trans-3-hexene | 0.006 | 0.003 | 0.667 | 0 |
| NMP | 0 | 0.98 | 0 | 1 |
| Mole Flow, lbmol/hr | | | | |
| 1-hexene | 11.645 | 0.004 | 0 | 0 |
| cis-2-hexene | 0.001 | 0.05 | 0 | 0 |
| trans-2-hexene | 0.002 | 0.037 | 0 | 0 |
| cis-3-hexene | 0.046 | 0.007 | 3.957 | 0 |
| trans-3-hexene | 0.07 | 0.021 | 7.925 | 0 |
| NMP | 0 | 5.044 | 0 | 5.044 |
| Mole Fraction | | | | |
| 1-hexene | 0.99 | 0.001 | 0 | 0 |
| cis-2-hexene | 0 | 0.01 | 0 | 0 |
| trans-2-hexene | 0 | 0.007 | 0 | 0 |
| cis-3-hexene | 0.004 | 0.001 | 0.333 | 0 |
| trans-3-hexene | 0.006 | 0.004 | 0.667 | 0 |
| NMP | 0 | 0.977 | 0 | 1 |
| Liquid Volume 16° C. (60° F.), cuft/hr | | | | |
| 1-hexene | 23.218 | 0.008 | 0 | 0 |
| cis-2-hexene | 0.001 | 0.097 | 0 | 0 |
| trans-2-hexene | 0.003 | 0.073 | 0 | 0 |
| cis-3-hexene | 0.092 | 0.014 | 7.811 | 0 |
| trans-3-hexene | 0.138 | 0.042 | 15.705 | 0 |
| NMP | 0 | 7.805 | 0 | 7.805 |
| Liquid Fraction 16° C. (60° F.) | | | | |
| 1-hexene | 0.99 | 0.001 | 0 | 0 |
| cis-2-hexene | 0 | 0.012 | 0 | 0 |
| trans-2-hexene | 0 | 0.009 | 0 | 0 |
| cis-3-hexene | 0.004 | 0.002 | 0.332 | 0 |
| trans-3-hexene | 0.006 | 0.005 | 0.668 | 0 |
| NMP | 0 | 0.971 | 0 | 1 |

The use of NMP resulted in a decrease in column diameter of ~14% compared to the case in Example 2, which did not include the use of an extractive distillation solvent. In addition, the use of NMP allowed the operating pressure to be reduced from 9 to 5 atm.

Example 7

Production of 1-hexene from 3-hexene using DMF to Improve 1-hexene Separation via Extractive Distillation The 3-hexene feedstock was assumed to have a composition of 33 wt % cis-3-hexene and 67 wt % trans-3-hexene. The normal boiling points for 1-, 2-, and 3-hexene are listed in Example 2. The normal boiling for DMF, the extraction solvent in this example, is 152° C. (305° F.). The isomerization reaction was assumed to occur at the bottom of the column. The column was assumed to have 150 theoretical stages, a kettle reboiler, and a total condenser. The operating conditions for the column consisted of a pressure of 7 atm, condenser temperature of 140° C. (283° F.), and reboiler temperature of 232° C. (450° F.). In addition, 100 lb/hr of DMF was added to the 10th theoretical stage of the column (near the top). This resulted in a column with a diameter of 11.8 ft and a reflux ratio of 518. For this case, the 1000 lb/hr 3-hexene feed resulted in 980 lb/hr of 99 wt % 1-hexene product. The column bottoms contained 91 wt % DMF, which can be recycled back to the column. A detailed material balance is shown in the following table. RXFEED is the distillation column feed stream, SOLVENT is the DMF extractive distillation solvent stream, BOTTOMS is the distillation column bottoms stream, and 1-HEXENE is the product stream, which is obtained from the top of the column.

Aspen material balance for 1-hexene production using DMF for extractive distillation (150 stage case).

| | Stream | | | |
|---|---|---|---|---|
| | 1-HEXENE | BOTTOMS | RXFEED | SOLVENT |
| Temperature, °C. (°F.) | 140 (283) | 232 (450) | 212 | 212 |
| Pressure, psi | 102.87 | 102.87 | 14.7 | 14.7 |
| Vapor Fraction | 0 | 0 | 1 | 0 |
| Mole Flow, lbmol/hr | 11.763 | 1.487 | 11.882 | 1.368 |
| Mass Flow, lb/hr | 990 | 110 | 1000 | 100 |
| Volume Flow, cuft/hr | 29.157 | 2.85 | 5673.407 | 2.067 |
| Enthalpy, MMBtu/hr | −0.248 | −0.12 | −0.213 | −0.133 |
| Mass Flow, lb/hr | | | | |
| 1-hexene | 979.997 | 0.272 | 0 | 0 |
| cis-2-hexene | 0.104 | 4.182 | 0 | 0 |
| trans-2-hexne | 0.117 | 3.167 | 0 | 0 |
| cis-3-hexene | 2.863 | 0.559 | 333 | 0 |
| trans-3-hexene | 6.92 | 1.82 | 667 | 0 |
| DMF | 0 | 100 | 0 | 100 |
| Mass Fraction | | | | |
| 1-hexene | 0.99 | 0.002 | 0 | 0 |
| cis-2-hexene | 0 | 0.038 | 0 | 0 |
| trans-2-hexne | 0 | 0.029 | 0 | 0 |
| cis-3-hexene | 0.003 | 0.005 | 0.333 | 0 |
| trans-3-hexene | 0.007 | 0.017 | 0.667 | 0 |
| DMF | 0 | 0.909 | 0 | 1 |
| Mole Flow, lbmol/hr | | | | |
| 1-hexene | 11.644 | 0.003 | 0 | 0 |
| cis-2-hexene | 0.001 | 0.05 | 0 | 0 |
| trans-2-hexne | 0.001 | 0.038 | 0 | 0 |
| cis-3-hexene | 0.034 | 0.007 | 3.957 | 0 |
| trans-3-hexene | 0.082 | 0.022 | 7.925 | 0 |
| DMF | 0 | 1.368 | 0 | 1.368 |
| Mole Fraction | | | | |
| 1-hexene | 0.99 | 0.002 | 0 | 0 |
| cis-2-hexene | 0 | 0.033 | 0 | 0 |
| trans-2-hexne | 0 | 0.025 | 0 | 0 |
| cis-3-hexene | 0.003 | 0.004 | 0.333 | 0 |
| trans-3-hexene | 0.007 | 0.015 | 0.667 | 0 |
| DMF | 0 | 0.92 | 0 | 1 |
| Liquid Volume 16° C. (60° F.), cuft/hr | | | | |
| 1-hexene | 23.217 | 0.006 | 0 | 0 |
| cis-2-hexene | 0.002 | 0.097 | 0 | 0 |
| trans-2-hexne | 0.003 | 0.075 | 0 | 0 |
| cis-3-hexene | 0.067 | 0.013 | 7.811 | 0 |
| trans-3-hexene | 0.163 | 0.043 | 15.705 | 0 |
| DMF | 0 | 1.696 | 0 | 1.696 |
| Liquid Fraction 16° C. (60° F.) | | | | |
| 1-hexene | 0.99 | 0.003 | 0 | 0 |
| cis-2-hexene | 0 | 0.05 | 0 | 0 |
| trans-2-hexne | 0 | 0.039 | 0 | 0 |
| cis-3-hexene | 0.003 | 0.007 | 0.332 | 0 |
| trans-3-hexene | 0.007 | 0.022 | 0.668 | 0 |
| DMF | 0 | 0.879 | 0 | 1 |

The use of DMF resulted in a decrease in column diameter of ~11% compared to the case in Example 2.

In addition to a potential reduction in column diameter, the use of DMF (or other extraction solvents) has the potential to reduce the number of stages (which is equivalent to a reduction in column height). The simulation model was used to determine the number of stages that would be required to achieve the same product quality in the same diameter column for Example 2 (13.2 ft). A series of cases were evaluated by considering different numbers of theoretical stages ranging from 110 to 150. The results are shown in the following table.

Sensitivity of the number of column stages required to achieve equivalent diameter to Example 2.

| Case | Number of Stages | Reflux Ratio | Column Diameter (ft) | Comment |
|---|---|---|---|---|
| 1 | 150 | 518 | 11.8 | Base case with DMF at 100 lb/hr |
| 2 | 140 | 536 | 12 | |
| 3 | 130 | 560 | 12.3 | |
| 4 | 120 | 613 | 12.9 | |
| 5 | 118 | 640 | 13.2 | Equivalent diameter to no DMF case |
| 6 | 115 | 668 | 13.6 | |
| 7 | 110 | 768 | 14.7 | |

For simulation Case 5 that considered 118 theoretical stages, a detailed material balance is shown in the table below. RXFEED is the distillation column feed stream, SOLVENT is the DMF extractive distillation solvent stream, BOT- TOMS is the distillation column bottoms stream, and 1-HEXENE is the product stream, which is obtained from the top of the column.

Aspen material balance for 1-hexene production using DMF for extractive distillation (118 stage case).

| | Stream | | | |
|---|---|---|---|---|
| | 1-HEXENE | BOTTOMS | RXFEED | SOLVENT |
| Temperature, °C. (° F.) | 146 (295) | 241 (466) | 100 (212) | 100 (212) |
| Pressure, psi | 117.57 | 117.57 | 14.7 | 14.7 |
| Vapor Fraction | 0 | 0 | 1 | 0 |
| Mole Flow, lbmol/hr | 11.763 | 1.487 | 11.882 | 1.368 |
| Mass Flow, lb/hr | 990 | 110 | 1000 | 100 |
| Volume Flow, cuft/hr | 29.669 | 2.903 | 5673.407 | 2.067 |
| Enthalpy, MMBtu/hr | −0.24 | −0.119 | −0.213 | −0.133 |
| Mass Flow, lb/hr | | | | |
| 1-hexene | 980.087 | 0.285 | 0 | 0 |
| cis-2-hexene | 0.34 | 4.17 | 0 | 0 |
| trans-2-hexne | 0.29 | 3.147 | 0 | 0 |
| cis-3-hexene | 2.452 | 0.573 | 333 | 0 |
| trans-3-hexene | 6.831 | 1.826 | 667 | 0 |
| DMF | 0 | 100 | 0 | 100 |
| Mass Fraction | | | | |
| 1-hexene | 0.99 | 0.003 | 0 | 0 |
| cis-2-hexene | 0 | 0.038 | 0 | 0 |
| trans-2-hexne | 0 | 0.029 | 0 | 0 |
| cis-3-hexene | 0.002 | 0.005 | 0.333 | 0 |
| trans-3-hexene | 0.007 | 0.017 | 0.667 | 0 |
| DMF | 0 | 0.909 | 0 | 1 |
| Mole Flow, lbmol/hr | | | | |
| 1-hexene | 11.645 | 0.003 | 0 | 0 |
| cis-2-hexene | 0.004 | 0.05 | 0 | 0 |
| trans-2-hexne | 0.003 | 0.037 | 0 | 0 |
| cis-3-hexene | 0.029 | 0.007 | 3.957 | 0 |
| trans-3-hexene | 0.081 | 0.022 | 7.925 | 0 |
| DMF | 0 | 1.368 | 0 | 1.368 |
| Mole Fraction | | | | |
| 1-hexene | 0.99 | 0.002 | 0 | 0 |
| cis-2-hexene | 0 | 0.033 | 0 | 0 |
| trans-2-hexne | 0 | 0.025 | 0 | 0 |
| cis-3-hexene | 0.002 | 0.005 | 0.333 | 0 |
| trans-3-hexene | 0.007 | 0.015 | 0.667 | 0 |
| DMF | 0 | 0.92 | 0 | 1 |
| Liquid Volume 16° C. (60° F.), cuft/hr | | | | |
| 1-hexene | 23.219 | 0.007 | 0 | 0 |
| cis-2-hexene | 0.008 | 0.097 | 0 | 0 |
| trans-2-hexne | 0.007 | 0.074 | 0 | 0 |
| cis-3-hexene | 0.058 | 0.013 | 7.811 | 0 |
| trans-3-hexene | 0.161 | 0.043 | 15.705 | 0 |
| DMF | 0 | 1.696 | 0 | 1.696 |
| Liquid Fraction 16° C. (60° F.) | | | | |
| 1-hexene | 0.99 | 0.003 | 0 | 0 |
| cis-2-hexene | 0 | 0.05 | 0 | 0 |
| trans-2-hexne | 0 | 0.038 | 0 | 0 |
| cis-3-hexene | 0.002 | 0.007 | 0.332 | 0 |
| trans-3-hexene | 0.007 | 0.022 | 0.668 | 0 |
| DMF | 0 | 0.879 | 0 | 1 |

In this case, at a pressure of 7 atm and with the addition of 100 lb/hr DMF, only 118 theoretical stages were required to achieve the same product quality (980 lb/hr, 99 wt % 1-hexene) with a 13.2 ft diameter column. Thus, the use of DMF can result in a decrease in the number of theoretical stages (proportional to column trays or height) of 21% compared to the case in Example 2. Similar results are expected for $C_4$ to $C_8$ alkenes.

Persons of ordinary skill in the art will recognize that many modifications may be made to the methods and compositions described in the present application without departing from the spirit and scope of the present application. The embodiment described herein is meant to be illustrative only and should not be taken as limiting the "invention," which is defined in the claims.

We claim:

1. A method for producing a distillation overhead comprising a 1-alkene comprising contacting a mixed alkene stream comprising said 1-alkene and homologs thereof with a supported isomerization catalyst under isomerization/distillation conditions effective to convert at least a portion of said homologs to said 1-alkene, said isomerization/distillation conditions also being effective to produce said distillation overhead comprising a sufficient portion of said 1-alkene to drive isomerization of said homologs to said 1-alkene while maintaining said mixed alkene stream at least partially in liquid phase, said isomerization/distillation conditions being effective to recover a quantity of 1-alkene greater than an equilibrium quantity of 1-alkene recovered under isomerization conditions alone, said 1-alkene being selected from the group consisting of 1-alkenes having from about 4 to about 8 carbon atoms; provided that said isomerization/distillation conditions comprise an amount of an extraction agent.

2. The method of claim 1 wherein said supported isomerization catalyst comprises an isomerization catalyst and a support, said support having substantially any morphology effective to expose a sufficient amount of said isomerization catalyst to said mixed alkenes to produce an effective reaction and flow through rate.

3. The method of claim 2 wherein said support is selected from the group consisting of extrudates, structured packing devices, monolithic supports, ceramic foams, and reticulated polymer foams comprising cells sufficiently large to prevent high pressure drops through the distillation column and to allow effective vapor flow.

4. The method of claim 2 wherein said support comprises a morphology selected from the group consisting of rings, saddles, balls, irregular, cylinders, multilobed structures, sheets, tubes, spirals, grills, packed bags, screens, ceramic foams, and reticulated polymer foams comprising cells sufficiently large to prevent high pressure drops through the distillation column and to allow effective vapor flow.

5. The method of claim 2 wherein said support is selected from the group consisting of $SiO_2$, $Al_2O_3$, ferrierite, and shape selective zeolites.

6. The method of claim 2 wherein said isomerization catalyst is selected from the group consisting of metals, metal oxides, bases, acids, bauxite, metal hydrides, and organoalkali compounds.

7. The method of claim 2 wherein said isomerization catalyst is selected from the group consisting of $K_2CO_3$, Pt, Pd, Ni, and combinations thereof.

8. The method of claim 6 wherein said isomerization catalyst is selected from the group consisting of $K_2CO_3$, Pt, Pd, Ni, and combinations thereof.

9. The method of claim 2 wherein said extraction agent is selected from the group consisting of amides, alcohols, aldehydes, ketones, alkyl carboxylates, amines, diamines, sulfolanes, and alkyl cyanides, each having from about 1 to about 20 carbon atoms.

10. The method of claim 2 wherein said extraction agent is N-methyl-2-pyrrolidone (NMP).

11. The method of claim 2 wherein said extraction agent is dimethyl formamide (DMF).

12. The method of claim 9 wherein
said alcohols are selected from the group consisting of MIBC (4-methyl-2-pentanol), n-butanol, isobutanol, and isoamyl alcohol (3-methyl-1-butanol);
said aldehyde is furfural;
said ketones are selected from the group consisting of acetophenone, dibutyl ketone (5-nonanone), isophorone, 2-pentanone and MIBK (methyl-isobutyl-ketone);
said alkyl carboxylates are selected from the group consisting of isovalerate, n-butyl formate, n-hexyl formate; t-butyl acetate, n-hexyl acetate;
said amine is diamylamine;
said diamine is ethylenediamine; and,
said alkyl cyanide is acetonitrile.

13. The method of claim 2 further comprising:
feeding said distillation overhead comprising said 1-alkene and a majority of homologous alkanes to a condenser; and
collecting at least a portion of said distillation overhead as 1-alkene product.

14. The method of claim 13 further comprising recycling a portion of said distillation overhead to said distillation column as reflux.

15. The method of claim 14 wherein said mixed alkene stream further comprises hydrogen.

16. The method of claim 14 wherein said mixed alkene stream is fed to a distillation column at a bottom of said distillation column.

17. The method of claim 16 further comprising recycling at least a portion of a bottoms stream back to said distillation column.

18. The method of claim 17 wherein said isomerization/distillation conditions comprise:
an operating pressure from about 0.01 atm to about 25 atm;
a condenser temperature from about −81° C. to about 254° C.;
a reboiler temperature from about −76° C. to about 263° C.; and,
a liquid hourly space velocity from about 0.1 $hr^{-1}$ to about 10 $hr^{-1}$.

19. The method of claim 18 wherein said feeding said mixed alkene stream comprises feeding at a liquid hourly space velocity of from about 1 $hr^{-1}$ to about 5 $hr^{-1}$.

20. A method for producing a distillation overhead comprising a 1-alkene comprising contacting a mixed alkene stream comprising said 1-alkene and homologs thereof with a supported isomerization catalyst under isomerization/distillation conditions effective to convert at least a portion of said homologs to said 1-alkene, said isomerization/distillation conditions also being effective to produce said distillation overhead comprising a sufficient portion of said 1-alkene to drive isomerization of said homologs to said 1-alkene while maintaining said mixed alkene stream at least partially in liquid phase, said isomerization/distillation conditions being effective to recover a quantity of 1-alkene greater than an equilibrium quantity of 1-alkene recovered under isomerization conditions alone, said 1-alkene being selected from the group consisting of 1-alkenes having from about 5 to about 8 carbon atoms; provided that said isomerization/distillation conditions comprise an amount of an extraction agent.

21. The method of claim 20 wherein said supported isomerization catalyst comprises an isomerization catalyst and a support, said support having substantially any morphology effective to expose a sufficient amount of said isomerization catalyst to said mixed alkenes to produce an effective reaction and flow through rate.

22. The method of claim 21 wherein said support is selected from the group consisting of extrudates, structured packing devices, monolithic supports, ceramic foams, and reticulated polymer foams comprising cells sufficiently large to prevent high pressure drops through the distillation column and to allow effective vapor flow.

23. The method of claim 21 wherein said support comprises a morphology selected from the group consisting of rings, saddles, balls, irregular, cylinders, multilobed structures, sheets, tubes, spirals, grills, packed bags, screens, ceramic foams, and reticulated polymer foams comprising cells sufficiently large to prevent high pressure drops through the distillation column and to allow effective vapor flow.

24. The method of claim 21 wherein said support is selected from the group consisting of $SiO_2$, $Al_2O_3$, ferrierite, and shape selective zeolites.

25. The method of claim 21 wherein said isomerization catalyst is selected from the group consisting of metals, metal oxides, bases, acids, bauxite, metal hydrides, and organoalkali compounds.

26. The method of claim 21 wherein said isomerization catalyst is selected from the group consisting of $K_2CO_3$, Pt, Pd, Ni, and combinations thereof.

27. The method of claim 24 wherein said isomerization catalyst is selected from the group consisting of metals, metal oxides, bases, acids, bauxite, metal hydrides, and organoalkali compounds.

28. The method of claim 24 wherein said isomerization catalyst is selected from the group consisting of $K_2CO_3$, Pt, Pd, Ni, and combinations thereof.

29. The method of claim 20 wherein said supported isomerization catalyst comprises an isomerization catalyst and a support, said support having substantially any morphology effective to expose a sufficient amount of said isomerization catalyst to said mixed alkenes to produce an effective reaction and flow through rate.

30. The method of claim 29 wherein said support is selected from the group consisting of extrudates, structured packing devices, monolithic supports, ceramic foams, and reticulated polymer foams comprising cells sufficiently large to prevent high pressure drops through the distillation column and to allow effective vapor flow.

31. The method of claim 29 wherein said support comprises a morphology selected from the group consisting of rings, saddles, balls, irregular, cylinders, multilobed structures, sheets, tubes, spirals, grills, packed bags, screens, ceramic foams, and reticulated polymer foams comprising cells sufficiently large to prevent high pressure drops through the distillation column and to allow effective vapor flow.

32. The method of claim 29 wherein said support is selected from the group consisting of $SiO_2$, $Al_2O_3$, ferrierite, and shape selective zeolites.

33. The method of claim 29 wherein said isomerization catalyst is selected from the group consisting of metals, metal oxides, bases, acids, bauxite, metal hydrides, and organoalkali compounds.

34. The method of claim 29 wherein said isomerization catalyst is selected from the group consisting of $K_2CO_3$, Pt, Pd, Ni, and combinations thereof.

35. The method of claim 30 wherein said isomerization catalyst is selected from the group consisting of metals, metal oxides, bases, acids, bauxite, metal hydrides, and organoalkali compounds.

36. The method of claim 30 wherein said isomerization catalyst is selected from the group consisting of $K_2CO_3$, Pt, Pd, Ni, and combinations thereof.

37. The method of claim 32 wherein said isomerization catalyst is selected from the group consisting of metals, metal oxides, bases, acids, bauxite, metal hydrides, and organoalkali compounds.

38. The method of claim 32 wherein said isomerization catalyst is selected from the group consisting of $K_2CO_3$, Pt, Pd, Ni, and combinations thereof.

39. The method of claim 29 wherein said extraction agent is effective to reduce a dimension selected from the group consisting of column diameter, number of stages, and a combination thereof, by 10% or more relative to the dimension required to achieve the same separation in the absence of said extraction agent.

40. The method of claim 29 wherein said extraction agent is effective to reduce a dimension selected from the group consisting of column diameter, number of stages, and a combination thereof, by 15% or more relative to the dimension required to achieve the same separation in the absence of said extraction agent.

41. The method of claim 29 wherein said extraction agent is effective to reduce a dimension selected from the group consisting of column diameter, number of stages, and a combination thereof, by 20% or more relative to the dimension required to achieve the same separation in the absence of said extraction agent.

42. The method of claim 29 wherein said extraction agent is selected from the group consisting of amides, alcohols, aldehydes, ketones, alkyl carboxylates, amines, diamines, sulfolanes, and alkyl cyanides, each having from about 1 to about 20 carbon atoms.

43. The method of claim 29 wherein said extraction agent is N-methyl-2-pyrrolidone (NMP).

44. The method of claim 29 wherein said extraction agent is dimethyl formamide (DMF).

45. The method of claim 42 wherein
said alcohols are selected from the group consisting of MIBC (4-methyl-2-pentanol), n-butanol, isobutanol, and isoamyl alcohol (3-methyl-1-butanol);
said aldehyde is furfural;
said ketones are selected from the group consisting of acetophenone, dibutyl ketone (5-nonanone), isophorone, 2-pentanone and MIBK (methyl-isobutyl-ketone);
said alkyl carboxylates are selected from the group consisting of isovalerate, n-butyl formate, n-hexyl formate; t-butyl acetate, n-hexyl acetate;
said amine is diamylamine;
said diamine is ethylenediamine; and,
said alkyl cyanide is acetonitrile.

46. The method of claim 29 further comprising:
feeding said distillation overhead comprising said 1-alkene and a majority of homologous alkanes to a condenser; and
collecting at least a portion of said distillation overhead as 1-alkene product.

47. The method of claim 46 further comprising recycling a portion of said distillation overhead to said distillation column as reflux.

48. The method of claim 47 wherein said mixed alkene stream further comprises hydrogen.

49. The method of claim 47 wherein said mixed alkene stream is fed to a distillation column at a bottom of said distillation column.

50. The method of claim 49 further comprising recycling at least a portion of a bottoms stream back to said distillation column.

51. The method of claim 29 wherein said isomerization/distillation conditions comprise:
an operating pressure of from about 0.01 atm to about 25 atm;
a condenser temperature of from about −55° C. to about 254° C.;
a reboiler temperature of from about −49° C. to about 263° C.; and,
a liquid hourly space velocity of from about 0.1 hr$^{-1}$ to about 10 hr$^{-1}$.

52. The method of claim 51 wherein said feeding said mixed alkene stream comprises feeding at a liquid hourly space velocity of from about 1 hr$^{-1}$ to about 5 hr$^{-1}$.

53. The method of claim 29 wherein, when said 1-alkene has from about 5 to about 6 carbon atoms.

54. The method of claim 52 wherein said operating pressure is from about 1 atm to about 15 atm.

55. The method of claim 52 wherein said operating pressure is from about 5 atm to about 13 atm.

56. A method for producing a distillation overhead comprising a 1-alkene comprising contacting a mixed alkene stream comprising said 1-alkene and homologs thereof with a supported isomerization catalyst under isomerization/distillation conditions effective to convert at least a portion of said homologs to said 1-alkene, said isomerization/distillation conditions also being effective to produce said distillation overhead comprising a sufficient portion of said 1-alkene to drive isomerization of said homologs to said 1-alkene while maintaining said mixed alkene stream at least partially in liquid phase, said isomerization/distillation conditions being effective to recover a quantity of 1-alkene greater than an equilibrium quantity of 1-alkene recovered under isomerization conditions alone, said 1-alkene being selected from the group consisting of 1-alkenes having from about 5 to about 6 carbon atoms; provided that said isomerization/distillation conditions comprise an amount of an extraction agent.

57. The method of claim 56 wherein said supported isomerization catalyst comprises an isomerization catalyst and a support, said support having substantially any morphology effective to expose a sufficient amount of said isomerization catalyst to said mixed alkenes to produce an effective reaction and flow through rate.

58. The method of claim 57 wherein said support is selected from the group consisting of extrudates, structured packing devices, monolithic supports, ceramic foams, and reticulated polymer foams comprising cells sufficiently large to prevent high pressure drops through the distillation column and to allow effective vapor flow.

59. The method of claim 57 wherein said support comprises a morphology selected from the group consisting of rings, saddles, balls, irregular, cylinders, multilobed structures, sheets, tubes, spirals, grills, packed bags, screens, ceramic foams, and reticulated polymer foams comprising cells sufficiently large to prevent high pressure drops through the distillation column and to allow effective vapor flow.

60. The method of claim 57 wherein said support is selected from the group consisting of $SiO_2$, $Al_2O_3$, ferrierite, and shape selective zeolites.

61. The method of claim 57 wherein said isomerization catalyst is selected from the group consisting of metals, metal oxides, bases, acids, bauxite, metal hydrides, and organoalkali compounds.

62. The method of claim 57 wherein said isomerization catalyst is selected from the group consisting of $K_2CO_3$, Pt, Pd, Ni, and combinations thereof.

63. The method of claim 58 wherein said isomerization catalyst is selected from the group consisting of metals, metal oxides, bases, acids, bauxite, metal hydrides, and organoalkali compounds.

64. The method of claim 58 wherein said isomerization catalyst is selected from the group consisting of $K_2CO_3$, Pt, Pd, Ni, and combinations thereof.

65. The method of claim 60 wherein said isomerization catalyst is selected from the group consisting of metals, metal oxides, bases, acids, bauxite, metal hydrides, and organoalkali compounds.

66. The method of claim 60 wherein said isomerization catalyst is selected from the group consisting of $K_2CO_3$, Pt, Pd, Ni, and combinations thereof.

67. The method of claim 56 wherein said supported isomerization catalyst comprises an isomerization catalyst and a support, said support having substantially any morphology effective to expose a sufficient amount of said isomerization catalyst to said mixed alkenes to produce an effective reaction and flow through rate.

68. The method of claim 67 wherein said support is selected from the group consisting of extrudates, structured packing devices, monolithic supports, ceramic foams, and reticulated polymer foams comprising cells sufficiently large to prevent high pressure drops through the distillation column and to allow effective vapor flow.

69. The method of claim 67 wherein said support comprises a morphology selected from the group consisting of rings, saddles, balls, irregular, cylinders, multilobed structures, sheets, tubes, spirals, grills, packed bags, screens, ceramic foams, and reticulated polymer foams comprising cells sufficiently large to prevent high pressure drops through the distillation column and to allow effective vapor flow.

70. The method of claim 67 wherein said support is selected from the group consisting of $SiO_2$, $Al_2O_3$, ferrierite, and shape selective zeolites.

71. The method of claim 67 wherein said isomerization catalyst is selected from the group consisting of metals, metal oxides, bases, acids, bauxite, metal hydrides, and organoalkali compounds.

72. The method of claim 67 wherein said isomerization catalyst is selected from the group consisting of $K_2CO_3$, Pt, Pd, Ni, and combinations thereof.

73. The method of claim 68 wherein said isomerization catalyst is selected from the group consisting of metals, metal oxides, bases, acids, bauxite, metal hydrides, and organoalkali compounds.

74. The method of claim 68 wherein said isomerization catalyst is selected from the group consisting of $K_2CO_3$, Pt, Pd, Ni, and combinations thereof.

75. The method of claim 70 wherein said isomerization catalyst is selected from the group consisting of metals, metal oxides, bases, acids, bauxite, metal hydrides, and organoalkali compounds.

76. The method of claim 70 wherein said isomerization catalyst is selected from the group consisting of $K_2CO_3$, Pt, Pd, Ni, and combinations thereof.

77. The method of claim 67 wherein said extraction agent is effective to reduce a dimension selected from the group consisting of the column diameter, the number of stages, and a combination thereof, by 10% or more relative to the dimension required to achieve the same separation in the absence of said extraction agent.

78. The method of claim 67 wherein said extraction agent is effective to reduce a dimension selected from the group consisting of the column diameter, the number of stages, and a combination thereof, by 15% or more relative to the dimension required to achieve the same separation in the absence of said extraction agent.

79. The method of claim 67 wherein said extraction agent is effective to reduce a dimension selected from the group consisting of the column diameter, the number of stages, and a combination thereof, by 20% or more relative to the dimension required to achieve the same separation in the absence of said extraction agent.

80. The method of claim 56 wherein said extraction agent is selected from the group consisting of amides, alcohols, aldehydes, ketones, alkyl carboxylates, amines, diamines, sulfolanes, and alkyl cyanides, each having from about 1 to about 20 carbon atoms.

81. The method of claim 56 wherein said extraction agent is N-methyl-2-pyrrolidone (NMP).

82. The method of claim 56 wherein said extraction agent is dimethyl formamide (DMF).

83. The method of claim 80 wherein
said alcohols are selected from the group consisting of MIBC (4-methyl-2-pentanol), n-butanol, isobutanol, and isoamyl alcohol (3-methyl-1-butanol);
said aldehyde is furfural;
said ketones are selected from the group consisting of acetophenone, dibutyl ketone (5-nonanone), isophorone, 2-pentanone and MIBK (methyl-isobutyl-ketone);
said alkyl carboxylates are selected from the group consisting of isovalerate, n-butyl formate, n-hexyl formate; t-butyl acetate, n-hexyl acetate;
said amine is diamylamine;
said diamine is ethylenediamine; and,
said alkyl cyanide is acetonitrile.

84. The method of claim 56 further comprising:
feeding said distillation overhead comprising said 1-alkene and a majority of homologous alkanes to a condenser; and
collecting at least a portion of said distillation overhead as 1-alkene product.

85. The method of claim 84 further comprising recycling a portion of said distillation overhead to said distillation column as reflux.

86. The method of claim 85 wherein said mixed alkene stream further comprises hydrogen.

87. The method of claim 85 wherein said mixed alkene stream is fed to a distillation column at a bottom of said distillation column.

88. The method of claim 87 further comprising recycling at least a portion of a bottoms stream back to said distillation column.

89. The method of claim 88 wherein said isomerization/distillation conditions comprise:
an operating pressure of from about 0.01 atm to about 25 atm;
a condenser temperature of from about −55° C. to about 192° C.;
a reboiler temperature of from about −49° C. to about 200° C.; and,
a liquid hourly space velocity of from about 0.1 $hr^{-1}$ to about 10 $hr^{-1}$.

90. The method of claim 89 wherein said feeding said mixed alkene stream comprises feeding at a liquid hourly space velocity of from about 1 hr$^{-1}$ to about 5 hr$^{-1}$.

91. The method of claim 90 wherein said operating pressure is from about 1 atm to about 15 atm.

92. The method of claim 90 wherein said operating pressure is from about 5 atm to about 13 atm.

93. The method of claim 90 wherein said operating pressure is from about 7 atm to about 10 atm.

94. A method for producing a distillation overhead comprising 1-butene comprising contacting a mixed C$_4$ stream comprising 2-butene, said 1-butene, and an amount of an extraction agent, with a supported isomerization catalyst under isomerization/distillation conditions comprising a condenser temperature of from about −81 to 35° C., a reboiler temperature of from about −76 to about 42° C., and a pressure of from about 0.01 to about 4 atm, for a period of time effective to convert a sufficient quantity of said 2-butene to said 1-butene to drive isomerization of said 2-butene to said 1-butene while maintaining said mixed alkene stream at least partially in liquid phase, said isomerization/distillation conditions being effective to recover a quantity of 1-butene greater than an equilibrium quantity of 1-butene recovered under isomerization conditions alone.

95. The method of claim 94 wherein said supported isomerization catalyst comprises an isomerization catalyst and a support, said support having substantially any morphology effective to expose a sufficient amount of said isomerization catalyst to said mixed alkenes to produce an effective reaction and flow through rate.

96. The method of claim 95 wherein said support is selected from the group consisting of SiO$_2$, Al$_2$O$_3$, ferrierite, and shape selective zeolites.

97. The method of claim 96 wherein said isomerization catalyst is selected from the group consisting of K$_2$CO$_3$, Pt, Pd, Ni, and combinations thereof.

98. The method of claim 95 wherein said extraction agent is effective to reduce a dimension selected from the group consisting of the column diameter, the number of stages, and a combination thereof, by 10% or more relative to the dimension required to achieve the same separation in the absence of said extraction agent.

99. The method of claim 95 wherein said extraction agent is effective to reduce a dimension selected from the group consisting of the column diameter, the number of stages, and a combination thereof, by 15% or more relative to the dimension required to achieve the same separation in the absence of said extraction agent.

100. The method of claim 95 wherein said extraction agent is effective to reduce a dimension selected from the group consisting of the column diameter, the number of stages, and a combination thereof, by 20% or more relative to the dimension required to achieve the same separation in the absence of said extraction agent.

101. The method of claim 95 wherein said extraction agent is selected from the group consisting of amides, alcohols, aldehydes, ketones, alkyl carboxylates, amines, diamines, sulfolanes, and alkyl cyanides, each having from about 1 to about 20 carbon atoms.

102. The method of claim 95 wherein said extraction agent is N-methyl-2-pyrrolidone (NMP).

103. The method of claim 95 wherein said extraction agent is dimethyl formamide (DMF).

104. The method of claim 95 wherein
said alcohols are selected from the group consisting of MIBC (4-methyl-2-pentanol), n-butanol, isobutanol, and isoamyl alcohol (3-methyl-1-butanol);
said aldehyde is furfural;
said ketones are selected from the group consisting of acetophenone, dibutyl ketone (5-nonanone), isophorone, 2-pentanone and MIBK (methyl-isobutyl-ketone);
said alkyl carboxylates are selected from the group consisting of isovalerate, n-butyl formate, n-hexyl formate; t-butyl acetate, n-hexyl acetate;
said amine is diamylamine;
said diamine is ethylenediamine; and,
said alkyl cyanide is acetonitrile.

105. The method of claim 95 further comprising:
feeding said distillation overhead comprising said 1-alkene and a majority of homologous alkanes to a condenser; and
collecting at least a portion of said distillation overhead as 1-alkene product.

106. The method of claim 95 further comprising recycling a portion of said distillation overhead to said distillation column as reflux.

107. The method of claim 106 wherein said mixed alkene stream further comprises hydrogen.

108. The method of claim 106 wherein said mixed alkene stream is fed to a distillation column at a bottom of said distillation column.

109. The method of claim 108 further comprising recycling at least a portion of a bottoms stream back to said distillation column.

110. The method of claim 109 wherein said feeding said mixed alkene stream comprises feeding at a liquid hourly space velocity of from about 1 hr$^{-1}$ to about 2 hr$^{-1}$.

111. A method for producing a distillation overhead comprising 1-pentene comprising contacting a mixed C$_5$ stream comprising 1-pentene and one or more homologs thereof with a supported isomerization catalyst under isomerization/distillation conditions comprising a condenser temperature of from about −55 to 169° C., a reboiler temperature of from about −49 to about 176° C., and a pressure of from about 0.01 to about 25 atm, for a period of time effective to convert a sufficient quantity of said homologs to said 1-pentene to drive isomerization of said homologs to said 1-pentene while maintaining said mixed alkene stream at least partially in liquid phase, said isomerization/distillation conditions being effective to recover a quantity of 1-pentene greater than an equilibrium quantity of 1-pentene recovered under isomerization conditions alone; provided that said isomerization/distillation conditions comprise an amount of an extraction agent.

112. The method of claim 111 wherein said supported isomerization catalyst comprises an isomerization catalyst and a support, said support having substantially any morphology effective to expose a sufficient amount of said isomerization catalyst to said mixed alkenes to produce an effective reaction and flow through rate.

113. The method of claim 112 wherein said support is selected from the group consisting of SiO$_2$, Al$_2$O$_3$, ferrierite, and shape selective zeolites.

114. The method of claim 113 wherein said isomerization catalyst is selected from the group consisting of K$_2$CO$_3$, Pt, Pd, Ni, and combinations thereof.

115. The method of claim 111 wherein said supported isomerization catalyst comprises an isomerization catalyst and a support, said support having substantially any morphology effective to expose a sufficient amount of said isomerization catalyst to said mixed alkenes to produce an effective reaction and flow through rate.

116. The method of claim 115 wherein said support is selected from the group consisting of $SiO_2$, $Al_2O_3$, ferrierite, and shape selective zeolites.

117. The method of claim 116 wherein said isomerization catalyst is selected from the group consisting of $K_2CO_3$, Pt, Pd, Ni, and combinations thereof.

118. The method of claim 115 wherein said extraction agent is effective to reduce a dimension selected from the group consisting of the column diameter, the number of stages, and a combination thereof, by 10% or more relative to the dimension required to achieve the same separation in the absence of said extraction agent.

119. The method of claim 117 wherein said extraction agent is effective to reduce a dimension selected from the group consisting of the column diameter, the number of stages, and a combination thereof, by 15% or more relative to the dimension required to achieve the same separation in the absence of said extraction agent.

120. The method of claim 117 wherein said extraction agent is effective to reduce a dimension selected from the group consisting of the column diameter, the number of stages, and a combination thereof, by 20% or more relative to the dimension required to achieve the same separation in the absence of said extraction agent.

121. The method of claim 118 wherein said extraction agent is selected from the group consisting of amides, alcohols, aldehydes, ketones, alkyl carboxylates, amines, diamines, sulfolanes, and alkyl cyanides, each having from about 1 to about 20 carbon atoms.

122. The method of claim 115 wherein said extraction agent is N-methyl-2-pyrrolidone (NMP).

123. The method of claim 115 wherein said extraction agent is dimethyl formamide (DMF).

124. A method for producing a distillation overhead comprising 1-hexene comprising contacting a mixed $C_6$ stream comprising 1-hexene and one or more homologs thereof with a supported isomerization catalyst under isomerization/distillation conditions comprising a condenser temperature of from about −30 to 192° C., a reboiler temperature of from about −26 to about 200° C., and a pressure of from about 0.01 to about 18 atm, for a period of time effective to convert a sufficient quantity of said homologs to said 1-hexene to drive isomerization of said homologs to said 1-hexene while maintaining said mixed alkene stream at least partially in liquid phase, said isomerization/distillation conditions being effective to recover a quantity of 1-hexene greater than an equilibrium quantity of 1-hexene recovered under isomerization conditions alone; provided that said isomerization/distillation conditions comprise an amount of an extraction agent.

125. The method of claim 124 wherein said supported isomerization catalyst comprises an isomerization catalyst and a support, said support having substantially any morphology effective to expose a sufficient amount of said isomerization catalyst to said mixed alkenes to produce an effective reaction and flow through rate.

126. The method of claim 125 wherein said support is selected from the group consisting of $SiO_2$, $Al_2O_3$, ferrierite, and shape selective zeolites.

127. The method of claim 126 wherein said isomerization catalyst is selected from the group consisting of $K_2CO_3$, Pt, Pd, Ni, and combinations thereof.

128. The method of claim 124 wherein said supported isomerization catalyst comprises an isomerization catalyst and a support, said support having substantially any morphology effective to expose a sufficient amount of said isomerization catalyst to said mixed alkenes to produce an effective reaction and flow through rate.

129. The method of claim 128 wherein said support is selected from the group consisting of $SiO_2$, $Al_2O_3$, ferrierite, and shape selective zeolites.

130. The method of claim 129 wherein said isomerization catalyst is selected from the group consisting of $K_2CO_3$, Pt, Pd, Ni, and combinations thereof.

131. The method of claim 129 wherein said extraction agent is effective to reduce a dimension selected from the group consisting of the column diameter, the number of stages, and a combination thereof, by 10% or more relative to the dimension required to achieve the same separation in the absence of said extraction agent.

132. The method of claim 129 wherein said extraction agent is effective to reduce a dimension selected from the group consisting of the column diameter, the number of stages, and a combination thereof, by 15% or more relative to the dimension required to achieve the same separation in the absence of said extraction agent.

133. The method of claim 129 wherein said extraction agent is effective to reduce a dimension selected from the group consisting of the column diameter, the number of stages, and a combination thereof, by 20% or more relative to the dimension required to achieve the same separation in the absence of said extraction agent.

134. The method of claim 124 wherein said extraction agent is selected from the group consisting of amides, alcohols, aldehydes, ketones, alkyl carboxylates, amines, diamines, sulfolanes, and alkyl cyanides, each having from about 1 to about 20 carbon atoms.

135. The method of claim 124 wherein said extraction agent is N-methyl-2-pyrrolidone (NMP).

136. The method of claim 124 wherein said extraction agent is dimethyl formamide (DMF).

137. A method for producing a distillation overhead comprising 1-heptene comprising contacting a mixed $C_7$ stream comprising 1-heptene and one or more homologs thereof with a supported isomerization catalyst under isomerization/distillation conditions comprising a condenser temperature of from about −6 to 220° C., a reboiler temperature of from about −4 to about 227° C., and a pressure of from about 0.01 to about 15 atm, for a period of time effective to convert a sufficient quantity of said homologs to said 1-heptene to drive isomerization of said homologs to said 1-heptene while maintaining said mixed alkene stream at least partially in liquid phase, said isomerization/distillation conditions being effective to recover a quantity of 1-heptene greater than an equilibrium quantity of 1-heptene recovered under isomerization conditions alone; provided that said isomerization/distillation conditions comprise an amount of an extraction agent.

138. The method of claim 137 wherein said supported isomerization catalyst comprises an isomerization catalyst and a support, said support having substantially any morphology effective to expose a sufficient amount of said isomerization catalyst to said mixed alkenes to produce an effective reaction and flow through rate.

139. The method of claim 138 wherein said support is selected from the group consisting of $SiO_2$, $Al_2O_3$, ferrierite, and shape selective zeolites.

140. The method of claim 139 wherein said isomerization catalyst is selected from the group consisting of $K_2CO_3$, Pt, Pd, Ni, and combinations thereof.

141. The method of claim 137 wherein said supported isomerization catalyst comprises an isomerization catalyst and a support, said support having substantially any morphology effective to expose a sufficient amount of said isomerization catalyst to said mixed alkenes to produce an effective reaction and flow through rate.

142. The method of claim 141 wherein said support is selected from the group consisting of $SiO_2$, $Al_2O_3$, ferrierite, and shape selective zeolites.

143. The method of claim 142 wherein said isomerization catalyst is selected from the group consisting of $K_2CO_3$, Pt, Pd, Ni, and combinations thereof.

144. The method of claim 141 wherein said extraction agent is effective to reduce a dimension selected from the group consisting of the column diameter, the number of stages, and a combination thereof, by 10% or more relative to the dimension required to achieve the same separation in the absence of said extraction agent.

145. The method of claim 141 wherein said extraction agent is effective to reduce a dimension selected from the group consisting of the column diameter, the number of stages, and a combination thereof, by 15% or more relative to the dimension required to achieve the same separation in the absence of said extraction agent.

146. The method of claim 141 wherein said extraction agent is effective to reduce a dimension selected from the group consisting of the column diameter, the number of stages, and a combination thereof, by 20% or more relative to the dimension required to achieve the same separation in the absence of said extraction agent.

147. The method of claim 141 wherein said extraction agent is selected from the group consisting of amides, alcohols, aldehydes, ketones, alkyl carboxylates, amines, diamines, sulfolanes, and alkyl cyanides, each having from about 1 to about 20 carbon atoms.

148. The method of claim 141 wherein said extraction agent is N-methyl-2-pyrrolidone (NMP).

149. The method of claim 141 wherein said extraction agent is dimethyl formamide (DMF).

150. A method for producing a distillation overhead comprising 1-octene comprising contacting a mixed $C_8$ stream comprising 1-octene and one or more homologs thereof with a supported isomerization catalyst under isomerization/distillation conditions comprising a condenser temperature of from about 14 to 254° C., a reboiler temperature of from about 15 to about 263° C., and a pressure of from about 0.01 to about 15 atm, for a period of time effective to convert a sufficient quantity of said homologs to said 1-octene to drive isomerization of said homologs to said 1-octene while maintaining said mixed alkene stream at least partially in liquid phase, said isomerization/distillation conditions being effective to recover a quantity of 1-octene greater than an equilibrium quantity of 1-octene recovered under isomerization conditions alone; provided that said isomerization/distillation conditions comprise an amount of an extraction agent.

151. The method of claim 150 wherein said supported isomerization catalyst comprises an isomerization catalyst and a support, said support having substantially any morphology effective to expose a sufficient amount of said isomerization catalyst to said mixed alkenes to produce an effective reaction and flow through rate.

152. The method of claim 151 wherein said isomerization catalyst is supported on an alumina extrudate.

153. The method of claim 152 wherein said isomerization catalyst is selected from the group consisting of $K_2CO_3$, Pt, Pd, Ni, and combinations thereof.

154. The method of claim 150 wherein said supported isomerization catalyst comprises an isomerization catalyst and a support, said support having substantially any morphology effective to expose a sufficient amount of said isomerization catalyst to said mixed alkenes to produce an effective reaction and flow through rate.

155. The method of claim 154 wherein said isomerization catalyst is supported on an alumina extrudate.

156. The method of claim 155 wherein said isomerization catalyst is selected from the group consisting of $K_2CO_3$, Pt, Pd, Ni, and combinations thereof.

157. The method of claim 154 wherein said extraction agent is effective to reduce a dimension selected from the group consisting of the column diameter, the number of stages, and a combination thereof, by 10% or more relative to the dimension required to achieve the same separation in the absence of said extraction agent.

158. The method of claim 154 wherein said extraction agent is effective to reduce a dimension selected from the group consisting of the column diameter, the number of stages, and a combination thereof, by 15% or more relative to the dimension required to achieve the same separation in the absence of said extraction agent.

159. The method of claim 154 wherein said extraction agent is effective to reduce a dimension selected from the group consisting of the column diameter, the number of stages, and a combination thereof, by 20% or more relative to the dimension required to achieve the same separation in the absence of said extraction agent.

160. The method of claim 154 wherein said extraction agent is selected from the group consisting of amides, alcohols, aldehydes, ketones, alkyl carboxylates, amines, diamines, sulfolanes, and alkyl cyanides, each having from about 1 to about 20 carbon atoms.

161. The method of claim 154 wherein said extraction agent is N-methyl-2-pyrrolidone (NMP).

162. The method of claim 154 wherein said extraction agent is dimethyl formamide (DMF).

* * * * *